United States Patent
Lazarev et al.

(10) Patent No.: US 10,672,560 B2
(45) Date of Patent: *Jun. 2, 2020

(54) ELECTRO-POLARIZABLE COMPOUND AND CAPACITOR

(71) Applicant: Capacitor Sciences Incorporated, Menlo Park, CA (US)

(72) Inventors: Pavel Ivan Lazarev, Menlo Park, CA (US); Paul T. Furuta, Sunnyvale, CA (US); Barry K. Sharp, Redwood City, CA (US); Yan Li, Fremont, CA (US); Ian S.G. Kelly-Morgan, San Francisco, CA (US)

(73) Assignee: CAPACITOR SCIENCES INCORPORATED, Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/208,953

(22) Filed: Dec. 4, 2018

(65) Prior Publication Data

US 2019/0108944 A1 Apr. 11, 2019

Related U.S. Application Data

(60) Division of application No. 15/163,595, filed on May 24, 2016, now Pat. No. 10,153,087, which is a
(Continued)

(51) Int. Cl.
| | |
|---|---|
| *H01G 4/14* | (2006.01) |
| *C09B 5/62* | (2006.01) |
| *H01G 4/18* | (2006.01) |
| *C09B 57/08* | (2006.01) |
| *C07D 471/22* | (2006.01) |
| *H01G 4/005* | (2006.01) |

(Continued)

(52) U.S. Cl.
CPC .......... *H01G 4/14* (2013.01); *C07D 471/22* (2013.01); *C09B 5/008* (2013.01); *C09B 5/62* (2013.01); *C09B 57/08* (2013.01); *H01G 4/005* (2013.01); *H01G 4/18* (2013.01); *H01G 4/32* (2013.01)

(58) Field of Classification Search
None
See application file for complete search history.

(56) References Cited

U.S. PATENT DOCUMENTS

| | | |
|---|---|---|
| 3,407,394 A | 10/1968 | Hartke |
| 4,549,034 A | 10/1985 | Sato et al. |

(Continued)

FOREIGN PATENT DOCUMENTS

| | | |
|---|---|---|
| CA | 2074848 A1 | 2/1998 |
| CN | 1582506 A | 2/2005 |

(Continued)

OTHER PUBLICATIONS

Final Office Action for U.S. Appl. No. 14/919,337 dated May 1, (Year: 2017).*

(Continued)

*Primary Examiner* — Zinna Northington Davis
(74) *Attorney, Agent, or Firm* — BCF LLP

(57) ABSTRACT

An electro-polarizable compound having the following formula (I):

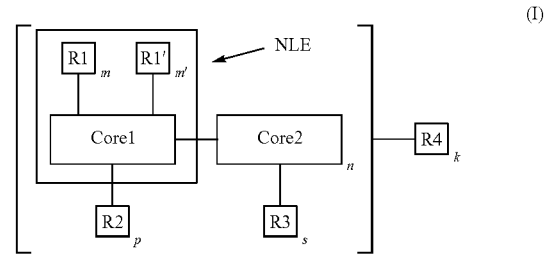

where Core1 is an aromatic polycyclic conjugated molecule having two-dimensional flat form and self-assembling by pi-pi stacking in a column-like supramolecule comprising one or more rylene fragments, R1 is an electron donor group connected to Core1 and R1' is an electron acceptor group connected to the Core1, m is number of acceptor group R1, m' is a number of donor group R', m and m' are equal to 0, 1, 2, 3, 4, 5 or 6, wherein m and m' are not both equal to 0, R2 is a substituent comprising one or more ionic groups from a class of ionic compounds that form ionic liquids connected to the Core1-directly or via a connecting group, p is a number of ionic groups R2 which is equal to 0, 1, 2, 3 or 4; wherein the fragment marked NLE containing the Core1 with at least one group R1 and/or R1' has a nonlinear effect of polarization, wherein Core2 is an electro-conductive oligomer, n is a number equal to 0, 2, or 4, R3 is a substituent comprising one or more ionic groups from a class of ionic compounds that form ionic liquids connected to the Core2 directly or via a connecting group, s is a number of the ionic groups R3 which is equal to 0, 1, 2, 3 or 4; wherein R4 is a non-conjugate cyclic or polycyclic resistive substituent electrically insulating the column-like supramolecules from each other and connected to the aromatic polycyclic conjugated molecule (Core1) and/or to the Core2 directly or via a connecting group, k is a number of substituents R4 which is equal to 1, 2, 3, 4, 5, 6, 7 or 8.

27 Claims, 1 Drawing Sheet

Related U.S. Application Data continuation-in-part of application No. 15/090,509, filed on Apr. 4, 2016, now Pat. No. 9,978,517.

(51) Int. Cl.
  *H01G 4/32* (2006.01)
  *C09B 5/00* (2006.01)

(56) References Cited

U.S. PATENT DOCUMENTS

| | | |
|---|---|---|
| 4,694,377 A | 9/1987 | MacDougall et al. |
| 4,702,562 A | 10/1987 | Scheuble et al. |
| 4,894,186 A | 1/1990 | Gordon et al. |
| 5,141,837 A | 8/1992 | Nguyen et al. |
| 5,187,639 A | 2/1993 | Ogawa et al. |
| 5,248,774 A | 9/1993 | Dietz et al. |
| 5,312,896 A | 5/1994 | Bhardwaj et al. |
| 5,384,521 A | 1/1995 | Coe |
| 5,395,556 A | 3/1995 | Drost et al. |
| 5,466,807 A | 11/1995 | Dietz et al. |
| 5,514,799 A | 5/1996 | Varanasi et al. |
| 5,581,437 A | 12/1996 | Sebillotte et al. |
| 5,583,359 A | 12/1996 | Ng et al. |
| 5,597,661 A | 1/1997 | Takeuchi et al. |
| 5,679,763 A | 10/1997 | Jen et al. |
| 5,742,471 A | 4/1998 | Barbee et al. |
| 5,840,906 A | 11/1998 | Zoltewicz et al. |
| 5,880,951 A | 3/1999 | Inaba |
| 6,025,094 A | 2/2000 | Visco et al. |
| 6,282,081 B1 | 8/2001 | Takabayashi et al. |
| 6,294,593 B1 | 9/2001 | Jeng et al. |
| 6,341,056 B1 | 1/2002 | Allman et al. |
| 6,391,104 B1 | 5/2002 | Schulz |
| 6,426,861 B1 | 7/2002 | Munshi |
| 6,501,093 B1 | 12/2002 | Marks |
| 6,519,136 B1 | 2/2003 | Chu et al. |
| 6,617,830 B2 | 9/2003 | Nozu et al. |
| 6,798,642 B2 | 9/2004 | Decker et al. |
| 7,025,900 B2 | 4/2006 | Sidorenko et al. |
| 7,033,406 B2 | 4/2006 | Weir et al. |
| 7,211,824 B2 | 5/2007 | Lazarev |
| 7,342,755 B1 | 3/2008 | Horvat et al. |
| 7,460,352 B2 | 12/2008 | Jamison et al. |
| 7,466,536 B1 | 12/2008 | Weir et al. |
| 7,498,689 B2 | 3/2009 | Mitani et al. |
| 7,579,709 B2 | 8/2009 | Goetz et al. |
| 7,625,497 B2 | 12/2009 | Iverson et al. |
| 7,750,505 B2 | 7/2010 | Ichikawa |
| 7,795,431 B2 | 9/2010 | Pschirer et al. |
| 7,808,771 B2 | 10/2010 | Nguyen et al. |
| 7,837,902 B2 | 11/2010 | Hsu et al. |
| 7,893,265 B2 | 2/2011 | Facchetti et al. |
| 7,910,736 B2 | 3/2011 | Koenemann et al. |
| 7,947,199 B2 | 5/2011 | Wessling |
| 7,990,679 B2 | 8/2011 | Ehrenberg et al. |
| 8,143,853 B2 | 3/2012 | Jestin et al. |
| 8,222,074 B2 | 7/2012 | Lazarev |
| 8,231,809 B2 | 7/2012 | Pschirer et al. |
| 8,236,998 B2 | 8/2012 | Nagata et al. |
| 8,344,142 B2 | 1/2013 | Marder et al. |
| 8,372,527 B2 | 2/2013 | Morishita et al. |
| 8,404,844 B2 | 3/2013 | Kastler et al. |
| 8,527,126 B2 | 9/2013 | Yamamoto et al. |
| 8,552,179 B2 | 10/2013 | Lazarev |
| 8,766,566 B2 | 7/2014 | Baba et al. |
| 8,818,601 B1 | 8/2014 | G V et al. |
| 8,831,805 B2 | 9/2014 | Izumi et al. |
| 8,895,118 B2 | 11/2014 | Geivandov et al. |
| 8,929,054 B2 | 1/2015 | Felten et al. |
| 8,938,160 B2 | 1/2015 | Wang |
| 9,056,676 B1 | 6/2015 | Wang |
| 9,293,260 B2 | 3/2016 | Schmid et al. |
| 9,589,727 B2 | 3/2017 | Lazarev |
| 9,899,150 B2 | 2/2018 | Lazarev |
| 9,916,931 B2 | 3/2018 | Lazarev |
| 9,978,517 B2 | 5/2018 | Lazarev et al. |
| 10,153,087 B2* | 12/2018 | Lazarev .................. C09B 5/008 |
| 2002/0027220 A1 | 3/2002 | Wang et al. |
| 2002/0048140 A1 | 4/2002 | Gallay et al. |
| 2003/0026063 A1 | 2/2003 | Munshi |
| 2003/0102502 A1 | 6/2003 | Togashi |
| 2003/0103319 A1 | 6/2003 | Kumar et al. |
| 2003/0105365 A1 | 6/2003 | Smith et al. |
| 2003/0142461 A1 | 7/2003 | Decker et al. |
| 2003/0160595 A1 | 8/2003 | Provanzana et al. |
| 2003/0219647 A1 | 11/2003 | Wariishi |
| 2004/0173873 A1 | 9/2004 | Kumar et al. |
| 2004/0222413 A1 | 11/2004 | Hsu et al. |
| 2004/0223291 A1 | 11/2004 | Naito et al. |
| 2005/0118083 A1 | 6/2005 | Tabuchi |
| 2006/0120014 A1 | 6/2006 | Nakamura et al. |
| 2006/0120020 A1 | 6/2006 | Dowgiallo |
| 2007/0001258 A1 | 1/2007 | Aihara |
| 2007/0108940 A1 | 5/2007 | Sainomoto et al. |
| 2007/0159767 A1 | 7/2007 | Jamison et al. |
| 2007/0181973 A1 | 8/2007 | Hung et al. |
| 2008/0002329 A1 | 1/2008 | Pohm et al. |
| 2008/0017850 A1 | 1/2008 | Koenemann et al. |
| 2008/0150484 A1 | 6/2008 | Kimball et al. |
| 2008/0266750 A1 | 10/2008 | Wu et al. |
| 2008/0283283 A1 | 11/2008 | Abe et al. |
| 2008/0283826 A1 | 11/2008 | Zheng et al. |
| 2009/0040685 A1 | 2/2009 | Hiemer et al. |
| 2009/0184355 A1 | 7/2009 | Brederlow et al. |
| 2010/0038629 A1 | 2/2010 | Lazarev |
| 2010/0085521 A1 | 4/2010 | Kasianova et al. |
| 2010/0172066 A1 | 7/2010 | Baer et al. |
| 2010/0173134 A1 | 7/2010 | Khokhlov et al. |
| 2010/0178728 A1 | 7/2010 | Zheng et al. |
| 2010/0183919 A1 | 7/2010 | Holme et al. |
| 2010/0193777 A1 | 8/2010 | Takahashi et al. |
| 2010/0214719 A1 | 8/2010 | Kim et al. |
| 2010/0233491 A1 | 9/2010 | Nokel et al. |
| 2010/0255381 A1 | 10/2010 | Holme et al. |
| 2010/0269731 A1 | 10/2010 | Jespersen et al. |
| 2010/0309606 A1 | 12/2010 | Allers et al. |
| 2010/0309696 A1 | 12/2010 | Guillot et al. |
| 2010/0315043 A1 | 12/2010 | Chau |
| 2011/0006393 A1 | 1/2011 | Cui |
| 2011/0042649 A1 | 2/2011 | Duvall et al. |
| 2011/0079733 A1 | 4/2011 | Langhals et al. |
| 2011/0079773 A1 | 4/2011 | Wasielewski et al. |
| 2011/0110015 A1 | 5/2011 | Zhang et al. |
| 2011/0228442 A1 | 9/2011 | Zhang et al. |
| 2012/0008251 A1 | 1/2012 | Yu et al. |
| 2012/0033342 A1 | 2/2012 | Ito et al. |
| 2012/0053288 A1 | 3/2012 | Morishita et al. |
| 2012/0056600 A1 | 3/2012 | Nevin |
| 2012/0059307 A1 | 3/2012 | Harris et al. |
| 2012/0113380 A1 | 5/2012 | Geivandov et al. |
| 2012/0122274 A1 | 5/2012 | Lazarev et al. |
| 2012/0244330 A1 | 9/2012 | Sun et al. |
| 2012/0268862 A1 | 10/2012 | Song et al. |
| 2012/0274145 A1 | 11/2012 | Taddeo |
| 2012/0302489 A1 | 11/2012 | Rodrigues et al. |
| 2013/0056720 A1 | 3/2013 | Kim et al. |
| 2013/0187475 A1 | 7/2013 | Vendik et al. |
| 2013/0194716 A1 | 8/2013 | Holme et al. |
| 2013/0215535 A1 | 8/2013 | Bellomo |
| 2013/0224473 A1 | 8/2013 | Tassell et al. |
| 2013/0314839 A1 | 11/2013 | Terashima et al. |
| 2013/0342967 A1 | 12/2013 | Lai et al. |
| 2014/0035100 A1 | 2/2014 | Cho |
| 2014/0036410 A1 | 2/2014 | Okamatsu et al. |
| 2014/0098458 A1 | 4/2014 | Almadhoun et al. |
| 2014/0158340 A1 | 6/2014 | Dixler et al. |
| 2014/0169104 A1 | 6/2014 | Kan et al. |
| 2014/0185260 A1 | 7/2014 | Chen et al. |
| 2014/0268490 A1 | 9/2014 | Tsai et al. |
| 2014/0316387 A1 | 10/2014 | Harris et al. |
| 2014/0347787 A1 | 11/2014 | Fathi et al. |
| 2015/0008671 A1 | 1/2015 | Rentero et al. |
| 2015/0008735 A1 | 1/2015 | Mizoguchi |
| 2015/0158392 A1 | 6/2015 | Zhao |

(56) References Cited

U.S. PATENT DOCUMENTS

| | | |
|---|---|---|
| 2015/0162131 A1 | 6/2015 | Felten et al. |
| 2015/0249401 A1 | 9/2015 | Eriksen et al. |
| 2015/0302990 A1 | 10/2015 | Ghosh et al. |
| 2016/0001662 A1 | 1/2016 | Miller et al. |
| 2016/0020026 A1 | 1/2016 | Lazarev |
| 2016/0020027 A1 | 1/2016 | Lazarev |
| 2016/0254092 A1 | 9/2016 | Lazarev et al. |
| 2016/0314901 A1 | 10/2016 | Lazarev |
| 2016/0340368 A1 | 11/2016 | Lazarev |
| 2016/0379757 A1 | 12/2016 | Robinson et al. |
| 2017/0117097 A1 | 4/2017 | Furuta et al. |
| 2017/0133167 A1 | 5/2017 | Keller et al. |
| 2017/0232853 A1 | 8/2017 | Lazarev et al. |
| 2017/0233528 A1 | 8/2017 | Sharp et al. |
| 2017/0236641 A1 | 8/2017 | Furuta et al. |
| 2017/0236642 A1 | 8/2017 | Furuta et al. |
| 2017/0236648 A1 | 8/2017 | Lazarev et al. |
| 2017/0237271 A1 | 8/2017 | Kelly-Morgan et al. |
| 2017/0237274 A1 | 8/2017 | Lazarev et al. |
| 2017/0287637 A1 | 10/2017 | Lazarev et al. |
| 2017/0287638 A1 | 10/2017 | Lazarev et al. |
| 2017/0301467 A1 | 10/2017 | Lazarev et al. |
| 2018/0033554 A1 | 2/2018 | Li et al. |
| 2018/0061582 A1 | 3/2018 | Furuta et al. |
| 2018/0122143 A1 | 5/2018 | Ellwood |
| 2018/0126857 A1 | 5/2018 | Kelly-Morgan |
| 2018/0137978 A1 | 5/2018 | Hein et al. |
| 2018/0137984 A1 | 5/2018 | Furuta et al. |
| 2018/0158616 A1 | 6/2018 | Lazarev et al. |

FOREIGN PATENT DOCUMENTS

| | | |
|---|---|---|
| CN | 100449661 | 1/2009 |
| CN | 1748271 B | 6/2010 |
| CN | 102426918 A | 4/2012 |
| CN | 103261370 A | 8/2013 |
| CN | 203118781 U | 8/2013 |
| CN | 203377785 U | 1/2014 |
| CN | 103755703 A | 4/2014 |
| CN | 103986224 A | 8/2014 |
| CN | 103258656 B | 8/2015 |
| DE | 10203918 A1 | 8/2003 |
| DE | 102010012949 A1 | 9/2011 |
| DE | 102011101304 A1 | 11/2012 |
| DE | 102012016438 A1 | 2/2014 |
| EP | 0443566 A1 | 8/1991 |
| EP | 0493716 A1 | 7/1992 |
| EP | 0585999 A1 | 3/1994 |
| EP | 0602654 A1 | 6/1994 |
| EP | 0729056 A1 | 8/1996 |
| EP | 0791849 A1 | 8/1997 |
| EP | 0986080 A3 | 1/2004 |
| EP | 0865142 B1 | 5/2008 |
| EP | 2062944 A1 | 5/2009 |
| EP | 2108673 A1 | 10/2009 |
| EP | 2415543 A1 | 2/2012 |
| EP | 1486590 B1 | 12/2013 |
| EP | 2759480 A1 | 7/2014 |
| EP | 1990682 B1 | 1/2015 |
| GB | 547853 A | 9/1942 |
| GB | 923148 A | 4/1963 |
| GB | 2084585 B | 11/1983 |
| JP | S6386731 A | 4/1988 |
| JP | H03253014 A | 11/1991 |
| JP | 2786298 B2 | 8/1998 |
| JP | 2000100484 A | 4/2000 |
| JP | 2001093778 A | 4/2001 |
| JP | 2007287829 A | 11/2007 |
| JP | 2010106225 A | 5/2010 |
| JP | 2010160989 A | 7/2010 |
| JP | 2011029442 A | 2/2011 |
| JP | 2014139296 A | 7/2014 |
| RU | 2199450 C1 | 2/2003 |
| RU | 2512880 C2 | 4/2014 |
| WO | 1990009616 A1 | 8/1990 |
| WO | 0139305 A1 | 5/2001 |
| WO | 2002026774 A2 | 4/2002 |
| WO | 2007078916 A2 | 7/2007 |
| WO | 2008038047 A2 | 4/2008 |
| WO | 2009101449 A2 | 8/2009 |
| WO | 2009144205 A1 | 12/2009 |
| WO | 2009158553 A2 | 12/2009 |
| WO | 2011056903 A1 | 5/2011 |
| WO | 2011137137 A1 | 11/2011 |
| WO | 2012012672 A2 | 1/2012 |
| WO | 2012084536 A1 | 6/2012 |
| WO | 2012122312 A1 | 9/2012 |
| WO | 2012142460 A1 | 10/2012 |
| WO | 2012162500 A2 | 11/2012 |
| WO | 2013009772 A1 | 1/2013 |
| WO | 2013085467 A1 | 6/2013 |
| WO | 2014009686 A1 | 1/2014 |
| WO | 2015003725 A1 | 1/2015 |
| WO | 2015175522 A1 | 11/2015 |
| WO | 2015175558 A2 | 11/2015 |

OTHER PUBLICATIONS

International Search Report and Written Opinion for International Application No. PCT/US2017/016862, dated Aug. 14, 2017.

International Search Report and Written Opinion for International Application No. PCT/US2017/017146, dated May 11, 2017.

International Search Report and Written Opinion for International Application No. PCT/US2017/017150, dated May 18, 2017.

International Search Report and Written Opinion for International Application No. PCT/US2017/24150, dated Jun. 21, 2017.

International Search Report and Written Opinion for International Application No. PCT/US2017/24371, dated Aug. 2, 2017.

International Search Report and Written Opinion for International Application No. PCT/US2017/24600, dated Aug. 14, 2017.

International Search Report and Written Opinion dated Feb. 23, 2018 for International Patent Application No. PCT/US17/64252.

International Search Report and Written Opinion dated Feb. 25, 2016 for International Application No. PCT/US15/58890, to Pavel Ivan Lazarev, filed Nov. 3, 2015.

International Search Report and Written Opinion dated Jul. 12, 2016 for International Application No. PCT/US2016/019641, to Pavel Ivan Lazarev, filed Feb. 25, 2016.

International Search Report and Written Opinion dated Jun. 7, 2017 for International Application No. PCT/US2017/24589, to Pavel Ivan Lazarev, filed Jun. 7, 2017.

International Search Report and Written Opinion dated Oct. 20, 2016 International Application No. PCT/US2016/039395, to Matthew R. Robinson, et al., filed Jun. 24, 2016.

International Search Report and Written Opinion dated Sep. 1, 2016 for International Application No. PCT/US2016/033628, to Pavel Ivan Lazarev, filed Sep. 1, 2016.

International Union of Pure and Applied Chemistry Polymer Divison Stejskal et al., "Polyaniline: Thin Films and Colloidal Dispersions (IUPAC Technical Report)", vol. 77, No. 5, pp. 815-826, Russian Academy of Sciences, St. Petersburg 199004, Russia; 2005.

Isoda, Kyosuke et al. "Truxene-Based Columnar Liquid Crystals: Self-Assembled Structures and Electro-Active Properties." Chemistry—An Asian Journal (2009), vol. 4, No. 10, pp. 1619-1625.

JACS Articles, Kang et. al., "Ultralarge Hyperpolarizability Twisted π-Electron System Electra-Optic Chromophores: Synthesis, Solid-State and Solution-Phase Structural Characteristics, Electronic Structures, Linear and Nonlinear Optical Properties, and Computational Studies", pp. 3267-3286; Perugia, Italy Feb. 20, 2007.

Jaroslav Stejskal and Irina Sapurina, "Polyaniline: Thin Films and Colloidal Dispersions (IUPAC Technical Report)", Pure and Applied Chemistry, vol. 77, No. 5, pp. 815-826 (2005).

Johnson, Kieth E. "What's an Ionic Liquid?" The Electrochemical Society Interface, Published Spring 2007, pp. 38-41, Accessed Aug. 28, 2017.

Kontrakt Technology Limited, Alla Sakharova, PhD., "Cryscade Solar Limited: Intellectual Property Portfolio summary", pp. 1-3, Cryscade Solar Limited; Apr. 9, 2015.

(56) References Cited

OTHER PUBLICATIONS

Li, Li-Li et al. "Synthesis and Mesomorphism of Ether-ester Mixed Tail C3-symmetrical Truxene discotic liquid crystals." Liquid Crystals(2010), vol. 37, No. 5, pp. 499-506.
Liang, Mao et al. "Synthesis and Photovoltaic Performance of Two Triarylamine Organic Dyes Based on Truxene." Yinyong Huaxue (2011) vol. 28 No. 12, pp. 1387-1392.
Lu, Meng et al. "Organic Dyes Incorporating Bis-hexapropyltruxeneamino Moiety for efficient Dye-sensitized Solar Cells." Journal of Physical Chemistry C (2011) vol. 115, No. 1, pp. 274-281.
M. Jurow et al, "Porphyrins as molectular electronic components of functional devices", Coordination Chemistry Reviews, Elsevier Science, Amsterdam NL, vol. 254, No. 19-20, Oct. 1, 2010, pp. 2297-2310.
Maddalena, Francesco "Why are Ionic Liquids, Liquids?" http://www.quora.com/why-are-ionic-liquids-liquids?, Published Jan. 26, 2017, Accessed Aug. 28, 2017.
Manukian, BK. 216. IR.-spektroskopische Untersuchungen in der Imidazol-Reihe. Helvetica Chimica Acta. 1965, vol. 48, p. 2001.
Microelectronics Research and Communications Institute, Founders et al., "High-Voltage Switching Circuit for Nanometer Scale CMOS Technologies", pp. 1-4, University of Idaho, Moscow, ID 83843 USA, Apr. 30, 2007.
Molecular Diversity Preservation International, Barber, et al. "Polymer Composite and Nanocomposite Dielectric Materials for Pulse Power Energy Storage" pp. 1-32; 29 University of South Carolina, Columbia, SC 29208 Oct. 2009.
Nagabrahmandachari et al. "Synthesis and Spectral Analysis of Tin Tetracarboxylates and Phosphinates" Indian Journal of Chemistry—Section A, 1995, vol. 34A, pp. 658-660.
Non-Final Action for U.S. Appl. No. 15/043,186, dated Feb. 14, 2018.
Non-Final Office Action dated Jun. 13, 2017 for U.S. Appl. No. 15/163,595.
Non-Final Office Action for U.S. Appl. No. 14/719,072, dated Aug. 2, 2017.
Non-Final Office Action for U.S. Appl. No. 15/043,247, dated Jun. 22, 2017.
Non-Final Office Action for U.S. Appl. No. 15/043,247, dated Jun. 7, 2018.
Non-Final Office Action for U.S. Appl. No. 15/043,315, dated Dec. 26, 2017.
Non-Final Office Action for U.S. Appl. No. 15/053,943, dated Apr. 19, 2017.
Non-Final Office Action for U.S. Appl. No. 15/090,509, dated Jun. 22, 2017.
Non-Final Office Action for U.S. Appl. No. 15/163,595, dated Jan. 17, 2018.
Non-Final Office Action for U.S. Appl. No. 15/194,224, dated Sep. 27, 2017.
Non-Final Office Action for U.S. Appl. No. 15/430,339, dated Jul. 11, 2018.
Non-Final Office Action for U.S. Appl. No. 15/430,307, dated Jul. 16, 2018.
Non-Final Office Action for U.S. Appl. No. 15/449,587, dated May 21, 2018.
Non-Final Office Action for U.S. Appl. No. 15/710,587, dated Jul. 3, 2018.
Non-Final Office Action for U.S. Appl. No. 15/782,752, dated Sep. 21, 2018.
Non-Final Office Action for U.S. Appl. No. 15/801,240, dated Oct. 19, 2018.
Non-Final Office Action for U.S. Appl. No. 15/805,016, dated Jun. 4, 2018.
Non-Final Office Action for U.S. Appl. No. 15/805,016, dated Month Day, Year.
Non-Final Office Action for U.S. Appl. No. 14/710,480, dated May 8, 2017.
Non-Final Office Action for U.S. Appl. No. 14/752,600, dated Jan. 23, 2017.
U.S. Appl. No. 62/121,328, to Pavel Ivan Lazarev et al., filed Feb. 26, 2015.
U.S. Appl. No. 62/294,949, to Pavel Ivan Lazarev, et al., filed Feb. 12, 2016.
U.S. Appl. No. 62/294,955, to Pavel Ivan Lazarev, et al., filed Feb. 12, 2016.
U.S. Appl. No. 62/294,964, to Pavel Ivan Lazarev, et al., filed Feb. 12, 2016.
U.S. Appl. No. 62/318,134, to Pavel Ivan Lazarev, et al., filed Mar. 4, 2016.
Updated Notice of Allowance for U.S. Appl. No. 14/710,480, dated Jan. 17, 2018.
Warmerdam, T. W. et al. "Discotic Liquid Crystals. Physical Parameters of some 2, 3, 7, 8, 12, 13-hexa(alkanoyloxy) truxenes: Observation of a Reentrant Isotropic Phase in a Pure Disk-like mesogen." Liquid Crystals (1988), vol. 3, No. 8, pp. 1087-1104.
Yue Wang, et. al., "Morphological and Dimensional Control via Hierarchical Assembly of Doped Oligoaniline Single Crystals", J. Am. Chem. Soc. 2012, 134, pp. 9251-9262.
Non-Final Office Action for U.S. Appl. No. 14/919,337, dated Jan. 4, 2017.
Non-Final Office Action for U.S. Appl. No. 15/043,186, dated Jun. 2, 2017.
Non-Final/Final Office Action for U.S. Appl. No. 15/043,247, dated Feb. 20, 2018.
Non-Final/Final Office Action for U.S. Appl. No. 15/430,391, dated Jul. 20, 2018.
Notice of Allowance for U.S. Appl. No. 14/710,480, dated Nov. 24, 2017.
Notice of Allowance for U.S. Appl. No. 14/710,480, dated Jan. 11, 2018.
Notice of Allowance for U.S. Appl. No. 14/710,480, dated Oct. 6, 2017.
Notice of Allowance for U.S. Appl. No. 14/710,491, dated Oct. 24, 2016.
Notice of Allowance for U.S. Appl. No. 14/719,072, dated Nov. 16, 2017.
Notice of Allowance for U.S. Appl. No. 14/752,600, dated Nov. 24, 2017.
Notice of Allowance for U.S. Appl. No. 14/752,600, dated Dec. 4, 2017.
Notice of Allowance for U.S. Appl. No. 14/752,600, dated Jul. 27, 2017.
Notice of Allowance for U.S. Appl. No. 14/919,337, dated Jul. 19, 2017.
Notice of Allowance for U.S. Appl. No. 14/919,337, dated Mar. 5, 2018.
Notice of Allowance for U.S. Appl. No. 14/919,337, dated Nov. 8, 2017.
Notice of Allowance for U.S. Appl. No. 14/931,757, dated Dec. 29, 2017.
Notice of Allowance for U.S. Appl. No. 14/931,757, dated Feb. 8, 2018.
Notice of Allowance for U.S. Appl. No. 14/931,757, dated Jul. 17, 2017.
Notice of Allowance for U.S. Appl. No. 14/931,757, dated Oct. 31, 2017.
Notice of Allowance for U.S. Appl. No. 15/053,943, dated Aug. 14, 2017.
Notice of Allowance for U.S. Appl. No. 15/090,509, dated Jan. 24, 2018.
Notice of Allowance for U.S. Appl. No. 15/163,595, dated Jul. 30, 2018.
Office Action dated May 18, 2018 for Chinese Patent Application for Invention No. 20158005110.
Office Action dated Dec. 13, 2017 for Taiwan Patent Application No. 106104499.
Office Action dated Dec. 13, 2017 for Taiwan Patent Application No. 106104500.
Office Action dated Jan. 25, 2018 for Chinese patent application No. 20158005146.4.

(56) References Cited

OTHER PUBLICATIONS

Office Action dated Oct. 19, 2017 for Taiwan patent Application No. 106104501.
Optical Society of America, Kuzyk et al, "Theory of Molecular Nonlinear Optics", pp. 5, 4-82, Department of Physics and Astronomy, Washington State University, Pullman, Washington 99164-2814, USA, Mar. 26, 2013.
Philosophical Transactions of the Royal Society, SIMON, "Charge storage mechanism in nanoporous carbons and its consequence for electrical double layer capacitors" pp. 3457-3467; Drexel University, Philadelphia, PA 19104, 2010.
PUBCHEM Open Chemistry Database, Compound Summary for CID 91001799. Mar. 17, 2015. pp. 1-10.
R. J. Baker and B. P. Johnson, "stacking power MOSFETs for use in high speed instrumentation", Department of Electrical Engineering, University of Nevada, Reno, Reno. Nevada 89557-0030; pp. 5799-5801 Aug. 3, 1992.
Roger D. Hartman and Herbert A. Pohl, "Hyper-electronic Polarization in Macromolecular Solids", Journal of Polymer Science: Part A-1, vol. 6, pp. 1135-1152 (1968).
RSC Publishing, Akl et al., "Molecular materials for switchable nonlinear optics in the solid state, based on ruthenium-nitrosyl complexes", pp. 3518-3527, Porto Alegre, Brazil; May 24, 2013.
Search Report and Written Opinion dated Feb. 7, 2018 for Singapore Patent Application No. 11201609435W.
Taiwan Office Action for TW Application No. 106104501, dated Oct. 19, 2017.
Taiwanese Office Action for 886103 Application No. 106142206, dated Jul. 5, 2018.
Trevethan, Thomas et al. "Organic Molecules Reconstruct Nanostructures on Ionic Surfaces." Small (2011), vol. 7, No. 9, pp. 1264-1270.
U.S. Appl. No. 14/719,072, to Pavel Ivan Lazarev, filed May 21, 2015.
U.S. Appl. No. 14/752,600, to Matthew R. Robinson, et al., filed Jun. 26, 2015.
U.S. Appl. No. 14/919,337, to Paul T. Furuta, et al., filed Oct. 21, 2015.
U.S. Appl. No. 14/931,757, to Pavel Ivan Lazarev, et al., filed Nov. 3, 2015.
U.S. Appl. No. 15/043,186, to Paul T. Furuta, et al., filed Feb. 12, 2016.
U.S. Appl. No. 15/043,209, to Paul T. Furuta, et al., filed Feb. 12, 2016.
U.S. Appl. No. 15/043,247, to Barry K Sharp, et al., filed Feb. 12, 2016.
U.S. Appl. No. 15/043,315, to Ian S.G. Kelly-Morgan, filed Feb. 12, 2014.
U.S. Appl. No. 15/043,315, to Ivan S.G. Kelley-Morgan, filed Feb. 12, 2016.
U.S. Appl. No. 15/053,943, to Pavel Ivan Lazarev, et al., filed Mar. 14, 2016.
U.S. Appl. No. 15/090,509, to Pavel Ivan Lazarev, et al., filed Mar. 4, 2016.
Caitlin S. Sample et al., Modular synthesis of asymmetric rylene derivatives\, Journal of Material Chemistry C, Jan. 19, 2017, 1052-1056, 5 (5), Royal Society of Chemistry, London U.K.
Center for Dielectric Studies, Janosik, et al., "Ultra-High Energy Density Capacitors Through Improved Glass Technology", pp. 1-5 Center for Dielectric Studies Penn State University, dated 2004.
Chao-Hsien Ho et al., "High dielectric constant polyaniline/poly(acrylic acid) composites prepared by in situ polymerization", Synthetic Metals, vol. 158, pp. 630-637 (2008).
Congressional Research Service, Paul W. Parfomak, "Energy Storage for Power Grids and Electric Transportation: A Technology Assessment", pp. 87-94; Members and Committees of Congress; Mar. 27, 2012.
Co-Pending U.S. Appl. No. 15/194,224, to Lazarev et al., filed Jun. 27, 2016.

Co-Pending U.S. Appl. No. 15/368,171, to Lazarev et al., filed Dec. 2, 2016.
Co-Pending U.S. Appl. No. 15/430,307, to Lazarev et al, filed Feb. 10, 2017.
Co-Pending U.S. Appl. No. 15/449,587, to Lazarev et al., filed Mar. 3, 2017.
Co-Pending U.S. Appl. No. 15/675,614, to Kelly-Morgan, filed Aug. 11, 2017.
Co-Pending U.S. Appl. No. 15/710,587, to Li et al, filed Sep. 20, 2017.
Co-Pending U.S. Appl. No. 15/469,126, to Lazarev et al, filed Mar. 24, 2017.
D C Tiwari, et al: "Temperature dependent studies of electric and dielectric properties of polythiophene based nano composite", Indian Journal of Pure & Applied Physicsvol. 50, Jan. 2012. pp. 49-56.
Deily, Dielectric and Optical Characterization of Polar Polymeric Materials: Chromophore Entrained PMMA Thin Films, Thesis, 2008.
Department of Chemistry and Biochemistry, Hardy, et al. "Converting an Electrical Insulator into a Dielectric Capacitor: End-Capping Polystyrene with Oligoaniline"; pp. 799-807, Rensselaer Polytechnic Institute, Troy, New York 12180; Feb. 17, 2013.
Department of Chemistry, Ho et al., "High dielectric constant polyanilinelpoly(acrylic acid) composites prepared by in situ polymerization", pp. 630-637; National Taiwan University, Taipei, Taiwan, ROC, Apr. 15, 2008.
Deruiter, J. Resonance and Induction Tutorial. Auburn University—Principles of Drug Action 1 Course Material. Spring 2005, 19 pages.
Extended European Search Report . 15792494.5, dated Dec. 11, 2017.
Extended European Search Report dated Aug. 8, 2018 for European Patent Application No. 16756391.5.
Extended European Search Report dated Sep. 24, 2018 for European Patent Application No. 15856609.1.
Extended European Search Report dated Sep. 26, 2018 for European Patent Application No. 16797411.2.
Extended European Search Report for Application No. 15792405.1, dated Nov. 10, 2017.
Final Office Action dated Feb. 14, 2018 for U.S. Appl. No. 15/043,186.
Final Office Action for U.S. Appl. No. 15/043,247, dated Oct. 24, 2018.
Final Office Action for U.S. Appl. No. 15/043,247, dated Oct. 4, 2017.
Final Office Action for U.S. Appl. No. 15/043,249, dated Feb. 6, 2018.
Final Office Action for U.S. Appl. No. 15/043,315, dated Jun. 7, 2018.
Final Office Action for U.S. Appl. No. 15/194,224, dated Jan. 30, 2018.
Final Office Action for U.S. Appl. No. 15/449,587, dated Oct. 10, 2018.
Final Office Action for U.S. Appl. No. 15/710,587, dated Nov. 6, 2018.
Final Office Action for U.S. Appl. No. 14/919,337, dated May 1, 2017.
Handy, Scott T. "Ionic Liquids—Classes and Properties" Published Sep. 2011, Accessed Aug. 28, 2017, InTechweb.org.
Henna Ruuska et al., "A Density Functional Study on Dielectric Properties of Acrylic Acid Crafted Polypropylene", The Journal of Chemical Physics, vol. 134, p. 134904 (2011).
Hindawi Publishing Corporation, Chávez-Castillo et al, "Third-Order Nonlinear Optical Behavior of Novel Polythiophene Derivatives Functionalized with Disperse Red 19 Chromophore", pp. 1-11, International Journal of Polymer Science vol. 2015, Article ID 219361, Mar. 12, 2015.
Hindawi Publishing Corporation, González-Espasandín et al., "Fuel Cells: A Real Option for Unmanned Aerial Vehicles Propulsion", pp. 1-13, Torrej'on de Ardoz, 28850 Madrid, Spain Jan. 30, 2014.
Hindawi Publishing Corporation, Khalil Ahmed et al., "High dielectric constant polyaniline/poly(acrylic acid) composites prepared by in situ polymerization", pp. 630-637, University of the Punjab, New Campus, Lahore 54590, Oct. 17, 2015.

(56) References Cited

OTHER PUBLICATIONS

Hsing-Yang Tsai et al, "1,6- and 1,7-Regioisomers of Asymmetric and Symmetric Perylene Bisimides: Synthesis, Characterization and Optical Properties" Molecules, 2014, vol. 19, pp. 327-341.
Hsing-Yang Tsai et al, "Synthesis and optical properties of novel asymmetric perylene bisimides", Journal of Luminescence, Vole 149, pp. 103-111 (2014).
Institute of Transportation Studies, Burke, et al. "Review of the Present and Future Applications of Supercapacitors in Electric and Hybrid Vehicles", pp. 2-23 UC Davis ITS; Dec. 2014.
International Application No. PCT/US/15/58890, to Pavel Ivan Lazarev, et al., filed Nov. 3, 2015.
International Search Report and Written Opinion dated Jul. 31, 2017 for International Patent Application PCT/US2017/024589.
International Search Report and Written Opinion for International Application No. PCT/US2015/030356, dated Jul. 28, 2015.
International Search Report and Written Opinion for International Application No. PCT/US2015/030415, dated Nov. 4, 2015.
International Search Report and Written Opinion for International Application No. PCT/US2015/058890, dated Feb. 25, 2016.
International Search Report and Written Opinion for International Application No. PCT/US2016/019641, dated Jul. 12, 2016.
International Search Report and Written Opinion for International Application No. PCT/US2016/033628, dated Sep. 1, 2016.
International Search Report and Written Opinion for International Application No. PCT/US2016/039395, dated Oct. 20, 2016.
International Search Report and Written Opinion for International Application No. PCT/US2016/039395, dated Jul. 1, 2016.
International Search Report and Written Opinion for International Application No. PCT/US2016/57765, dated Jan. 5, 2017.
Ni, Hai-Lang et al., "Truxene Discotic Liquid Crystals with Two Different Ring Substituents: Synthesis, Metamorphosis and High Charged Carrier Mobility", Liquid Crystals, vol. 40, No. 3, pp. 411-420, Jan. 4, 2013.
Supplementary European Search Report issued in corresponding European patent application No. 17779545 dated Dec. 5, 2019.

* cited by examiner

ELECTRO-POLARIZABLE COMPOUND AND CAPACITOR

CLAIM OF PRIORITY

This application is a division of U.S. patent application Ser. No. 15/163,595, filed May 24, 2016, the entire contents of which are incorporated herein by reference. U.S. patent application Ser. No. 15/163,595 is a continuation-in-part of U.S. patent application Ser. No. 15/090,509 filed Apr. 4, 2016 (now U.S. Pat. No. 9,978,517), the entire contents of which are incorporated herein by reference.

FIELD OF THE INVENTION

The present disclosure relates generally to passive components of electrical circuit and more particularly to an electro-polarizable compound and capacitor based on this material and intended for energy storage.

BACKGROUND

A capacitor is a passive electronic component that is used to store energy in the form of an electrostatic field, and comprises a pair of electrodes separated by a dielectric layer. When a potential difference exists between the two electrodes, an electric field is present in the dielectric layer. An ideal capacitor is characterized by a single constant value of capacitance, which is a ratio of the electric charge on each electrode to the potential difference between them. For high voltage applications, much larger capacitors have to be used.

One important characteristic of a dielectric material is its breakdown field. The breakdown field corresponds to the value of electric field strength at which the material suffers a catastrophic failure and conducts electricity between the electrodes. For most capacitor geometries, the electric field in the dielectric can be approximated by the voltage between the two electrodes divided by the spacing between the electrodes, which is usually the thickness of the dielectric layer. Since the thickness is usually constant it is more common to refer to a breakdown voltage, rather than a breakdown field. There are a number of factors that can dramatically reduce the breakdown voltage. In particular, the geometry of the conductive electrodes is important factor affecting breakdown voltage for capacitor applications. In particular, sharp edges or points hugely increase the electric field strength locally and can lead to a local breakdown. Once a local breakdown starts at any point, the breakdown will quickly "trace" through the dielectric layer until it reaches the opposite electrode and causes a short circuit.

Breakdown of the dielectric layer usually occurs as follows. Intensity of an electric field becomes high enough to "pull" electrons from atoms of the dielectric material and makes them conduct an electric current from one electrode to another. Presence of impurities in the dielectric or imperfections of the crystal structure can result in an avalanche breakdown as observed in semiconductor devices.

Another important characteristic of a dielectric material is its dielectric permittivity. Different types of dielectric materials are used for capacitors and include ceramics, polymer film, paper, and electrolytic capacitors of different kinds. The most widely used polymer film materials are polypropylene and polyester. Increasing dielectric permittivity allows for increasing volumetric energy density, which makes it an important technical task.

Second-order nonlinear optical (NLO) effects of organic molecules have been extensively investigated for their advantages over inorganic crystals. Properties studied, for example, include their large optical non-linearity, ultra-fast response speed, high damage thresholds and low absorption loss, etc. Particularly, organic thin films with excellent optical properties have tremendous potential in integrated optics such as optical switching, data manipulation and information processing. Among organic NLO molecules, azo-dye chromophores have been a special interest to many investigators because of their relatively large molecular hyper-polarizability (b) due to delocalization of the p-electronic clouds. They were most frequently either incorporated as a guest in the polymeric matrix (guest-host polymers) or grafted into the polymeric matrix (functionalized polymers) over the past decade.

Hyper-electronic polarization of organic compounds is described in greater detail in Roger D. Hartman and Herbert A. Pohl, "Hyper-electronic Polarization in Macromolecular Solids", Journal of Polymer Science: Part A-1 Vol. 6, pp. 1135-1152 (1968). Hyper-electronic polarization may be viewed as the electrical polarization external fields due to the pliant interaction with the charge pairs of excitons, in which the charges are molecularly separated and range over molecularly limited domains. In this article four polyacene quinone radical polymers were investigated. These polymers at 100 Hz had dielectric constants of 1800-2400, decreasing to about 58-100 at 100,000 Hz. Essential drawback of the described method of production of material is use of a high pressure (up to 20 kbars) for forming the samples intended for measurement of dielectric constants.

SUMMARY

The present disclosure provides an electro-polarizable compound having the following general formula (I):

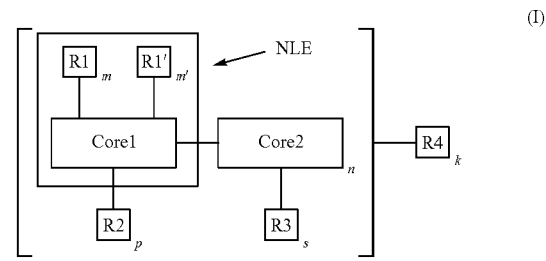

(I)

Core1 is an aromatic polycyclic conjugated molecule having two-dimensional flat form and self-assembling by pi-pi stacking in a column-like supramolecule, R1 are electron donor groups connected to the aromatic polycyclic conjugated molecule (Core1) and R1' are electron acceptor groups connected to the aromatic polycyclic conjugated molecule (Core1), m is number of acceptor groups R1, m' is a number of donor groups R', m and m' are equal to 0, 1, 2, 3, 4, 5 or 6, wherein m and m' are not both equal to 0, R2 is a substituent comprising one or more ionic groups from a class of ionic compounds that are used in ionic liquids connected to the aromatic polycyclic conjugated molecule (Core1) directly or via a connecting group, p is number of ionic groups R2 which is equal to 0, 1, 2, 3 or 4. The fragment marked NLE containing the Core1 with at least one group R1 and/or R1' has a nonlinear effect of polarization.

Core2 is an electro-conductive oligomer and number n of the electro-conductive oligomers is equal to 0, 2, or 4. R3 is a substituent comprising one or more ionic groups from a class of ionic compounds that are used in ionic liquids connected to the electro-conductive oligomer (Core2) directly or via a connecting group, s is number of the ionic groups R3 which is equal to 0, 1, 2, 3 or 4.

R4 is a resistive substituent providing solubility of the organic compound in a solvent and electrically insulating the column-like supramolecules from each other and connected to the aromatic polycyclic conjugated molecule (Core1) and/or to the electro-conductive oligomer (Core2) directly or via a connecting group. The parameter k is a number of substituents R4, which is equal to 0, 1, 2, 3, 4, 5, 6, 7 or 8.

In one aspect, the present disclosure provides a solution comprising an organic solvent and at least one disclosed electro-polarizable compound.

In another aspect, the present disclosure provides a crystal metadielectric layer comprising a mixture of the electro-polarizable compounds as disclosed above. The nonlinearly polarizable fragments comprising an aromatic polycyclic conjugated molecule with at least one group R1 are placed into the resistive dielectric envelope formed by resistive substituents R4 providing solubility of the organic compound in a solvent and electrically insulating the column-like supramolecules from each other.

In still another aspect, the present invention provides a meta-capacitor comprising two metal electrodes positioned parallel to each other and which can be rolled or flat and planar with said metadielectric layer between said electrodes, wherein the metadielectric layer comprises one or more types of the disclosed electro-polarizable. The nonlinearly polarizable fragments comprising an aromatic polycyclic conjugated molecule with at least one group R1, the electro-conductive oligomers and the ionic groups which have electronic and/or ionic type of polarizability are placed into the resistive dielectric envelope formed by resistive substituents providing solubility of the organic compound in a solvent and electrically insulating the column-like supramolecules from each other.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1A:
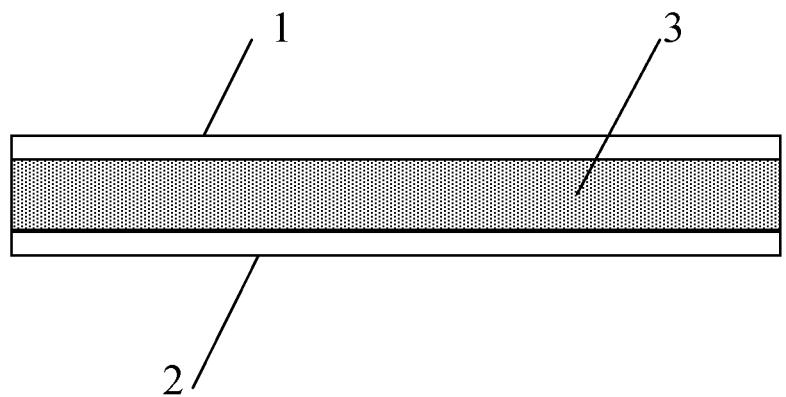
FIG. 1A schematically shows a capacitor with flat and planar electrodes in accordance with an aspect of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides an electro-polarizable compound. Existence of the electrophilic groups (acceptors) and the nucleophilic groups (donors) in the aromatic polycyclic conjugated molecule (Core1) promotes non-uniform distribution of electronic density in the conjugated molecule: surplus of electrons in one place (in a donor zone) and a shortage of electrons in other place (in an acceptor zone). The influence of external electric field onto non-uniform distribution of electronic density along the conjugated molecule leads to the induced polarization $P_{ind}$. In the general case the induced polarization is nonlinear function of intensity of local electric field $E_{loc}$. In the assumption of weak nonlinearity when it is possible to be limited to several members of decomposition of an induced polarization into a series on degrees of intensity of a local electric field, the induced polarization of the environment (of molecule) can be written down in the following form:

$$P_{ind} = \alpha \cdot E_{loc} + \beta \cdot E_{loc}^2 + \ldots,$$

where $\alpha$-linear polarizability, $\beta$-square polarizability. Though the assumption of a smallness of electric field is not always right, nevertheless parameters $\alpha$ and $\beta$ can be used for qualitative analysis of polarizability of the disclosed compounds. In the present disclosure the main attention is paid to ways of increase in the induced polarization of the disclosed compounds and therefore onto ways of increase of the linear polarizability $\alpha$ and square polarizability $\beta$. Such attention is caused by that the constant dipole and quadrupole electrical moments are mutually neutralized at self-assembly of such conjugated molecules. Analysis shows that linear polarizability depends on the size of the average electronic density in the molecule, and nonlinear polarizability depends on the size of heterogeneity of electronic density. It is also shown that a non-centrosymmetric arrangement of the electron donor and acceptor groups can lead to a strong nonlinear response of the compound's electronic polarization in the presence of an electric field. Influence of chemical structure on linear polarizability $\alpha$ and square polarizability $\beta$ is shown in Table 1 below.

TABLE 1

| chemical structure | $\alpha$ | $\beta$ |
|---|---|---|
| 1 | 945 | 0.041 |

TABLE 1-continued
| chemical structure | α | β |
|---|---|---|
| 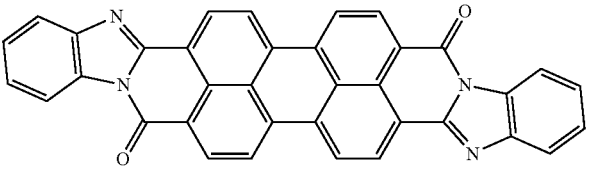<br>2 | 1348 | 0.165 |
| 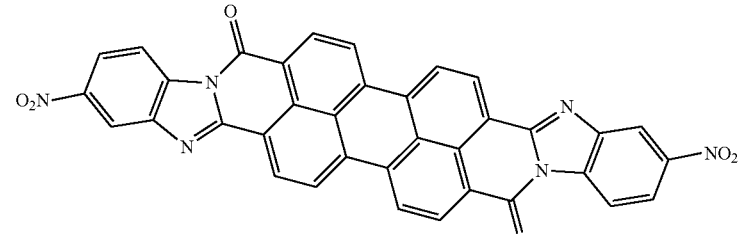<br>3 | 1537 | 862 |
| 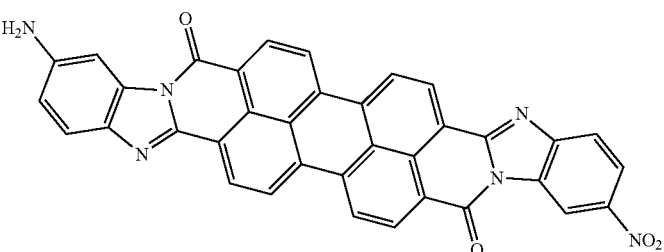<br>4 | 1252 | 21107 |
| 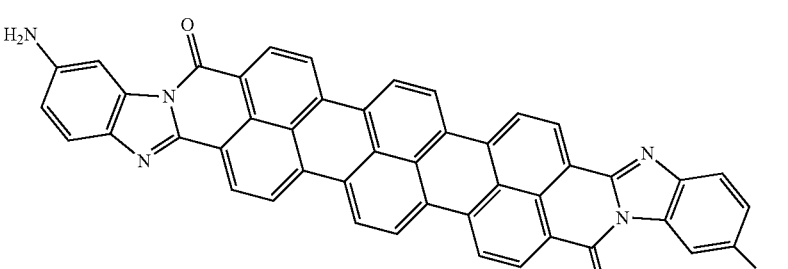<br>5 | 1908 | 40221 |
| 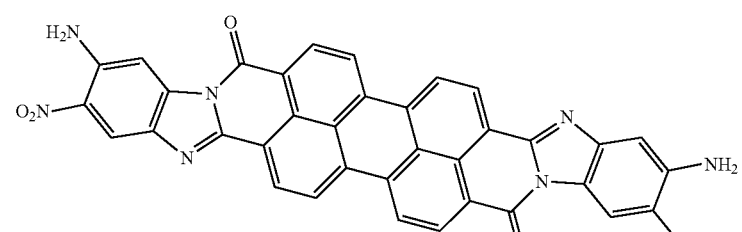<br>6 | 1431 | 35189 |

TABLE 1-continued

| chemical structure | α | β |
|---|---|---|
| 7 | 2057 | 168081 |
| 7 | 3397 | 582843 |
| 8 | 4604 | 1002570 |

An essential feature of the present disclosure is use of rigid no-conjugated limit carbon structures as resistive substituents. Such structures are absolutely determined in distinguishing from the dielectric structures formed by "fat" tails (such as alkyl, aryl, substituted alkyl, substituted aryl, fluorinated alkyl, chlorinated alkyl, branched and complex alkyl) which can be bent (curved) and lead to stochastic distribution of electronic density in the dielectric structure that leads to its electric breakdown. Thus, as resistive substituent R4 is used a non-conjugated compound, such as cyclo-hydrocarbons with rigid/fixed spatial structure like cyclohexane, cyclopentane and flat structures that are built as tiles from cyclo-molecules that do not contain voids/ empty space; that have dense packing of SP3 carbon with H and F substituts. Otherwise use of fat tails leads to formation of friable dielectric structure (film, layer, and envelope). It is possible that in friable structure always there will be a local area ("hole") in which electronic density is equal to zero and which can be occupied with a free electron (that leads to electric breakdown). It is possible to enter a concept of a molecular hole when one molecule "is taken out" from the ordered structure (from a crystal lattice). In this case the quantum object (a quantum hole, a quantum point) is formed in which there are empty (non-occupied) energy levels. Set of such objects creates a condition for conductivity of electrons and for electric breakdown of dielectric structure. Therefore in the present disclosure the determined structures forming the ordered crystal dielectric layers are disclosed which do not allow electrons to pass through material.

Presence of the electro-conductive oligomers leads to increasing of polarizability of the disclosed electro-polarizable compound because of electronic super conductivity of the electro-conductive oligomers. Ionic groups increase an ionic component of polarization of the disclosed electro-polarizable compound. The nonlinearly polarizable fragments comprising an aromatic polycyclic conjugated molecule with at least one dopant group, the electro-conductive oligomers and the ionic groups are placed into the resistive dielectric envelope formed by resistive substituents providing solubility of the organic compound in a solvent and electrically insulating the column-like supramolecules from each other. The resistive substituents increase the electric strength of these electro-polarizable compounds and breakdown voltage of the dielectric layers made on their basis.

In one embodiment of the present disclosure, the aromatic polycyclic conjugated molecule (Core1) comprises rylene fragments, which may be in conjugation with phenyl amides, naphthalene amides, and/or anthracene amides. In another embodiment of the disclosed electro-polarizable compound, the rylene fragments are selected from structures from 1 to 12 as given in Table 2.

TABLE 2

Examples of the aromatic polycyclic conjugated molecule comprising rylene fragments

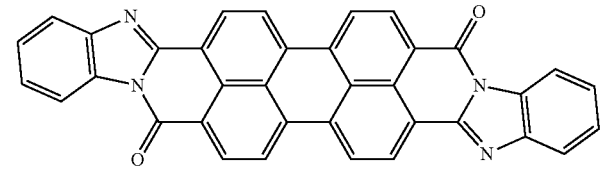 [SMILES: O=c1c2ccc3c4ccc5c6c(ccc(c7ccc(c2c37)c2nc3ccccc3n12)c46)c(=O)n1c2ccccc2nc51]
1

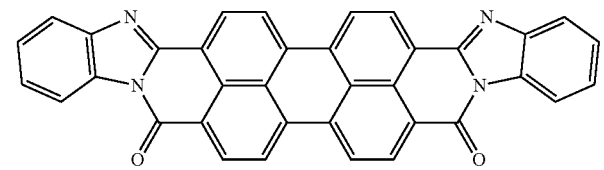 [SMILES: O=c1c2ccc3c4ccc5c(=O)n6c7ccccc7nc6c6ccc(c7ccc(c2c37)c2nc3ccccc3n12)c4c56]
2

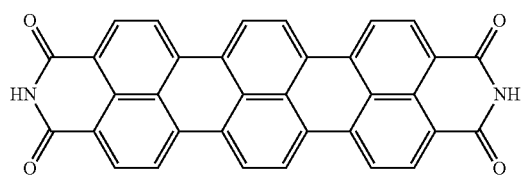
3

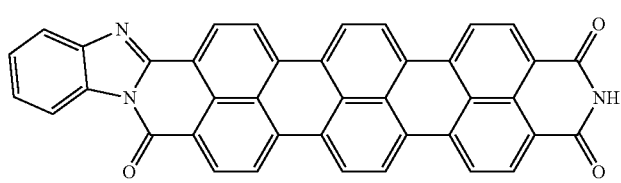 [SMILES: O=C1NC(=O)c2ccc3c4ccc5c6ccc7c8c(ccc(c9ccc(c%10ccc1c2c%103)c4c95)c68)c(=O)n1c2ccccc2nc71]
4

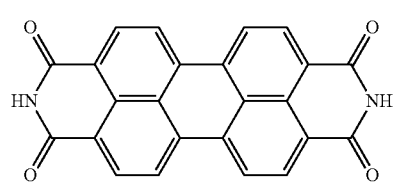 [SMILES: O=C1NC(=O)c2ccc3c4ccc5c6c(ccc(c7ccc1c2c73)c64)C(=O)NC5=O]
5

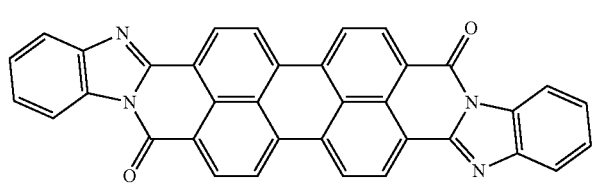 [SMILES: O=c1c2ccc3c4ccc5c6c(ccc(c7ccc(c2c37)c2nc3ccccc3n12)c46)c(=O)n1c2ccccc2nc51]
6

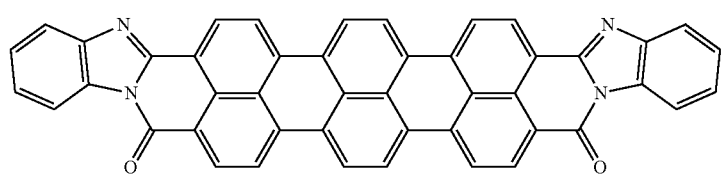 [SMILES: O=c1c2ccc3c4ccc5c6ccc7c(=O)n8c9ccccc9nc8c8ccc(c9ccc(c%10ccc(c2c3%10)c2nc3ccccc3n12)c4c59)c6c78]
7

TABLE 2-continued

Examples of the aromatic polycyclic conjugated molecule comprising rylene fragments

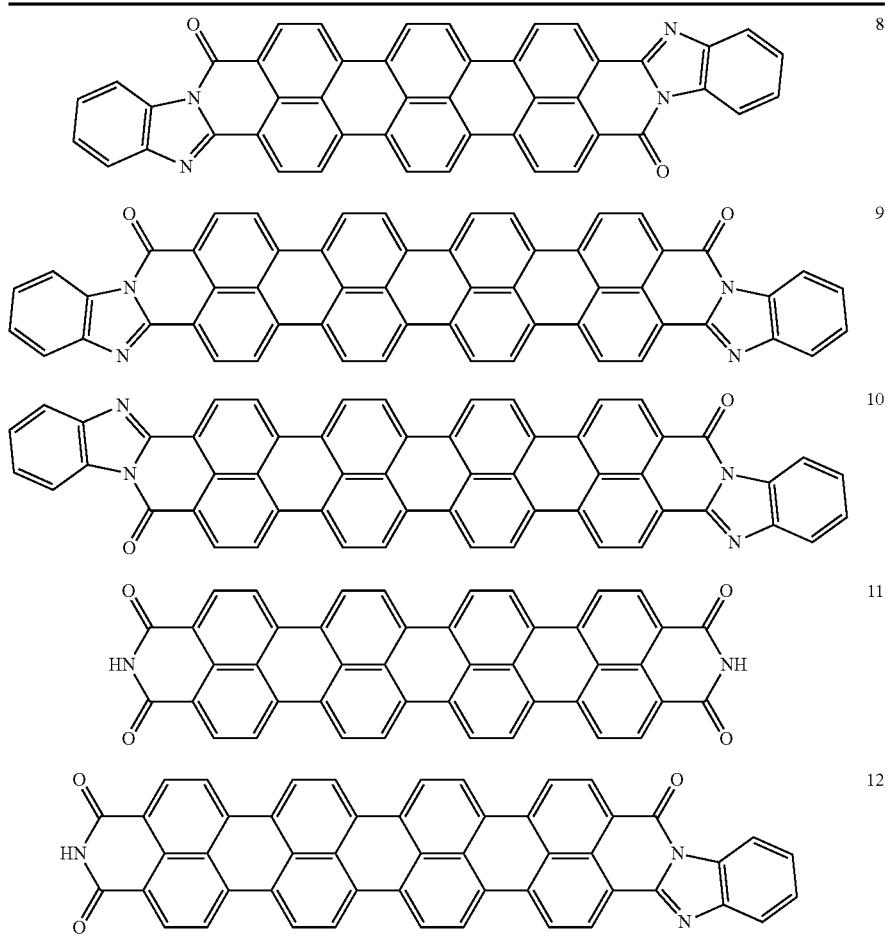

8

9

10

11

12

40

In one embodiment of the present disclosure, the electron donor and acceptor groups (R1) are selected from nucleophilic groups (donors) and electrophilic groups (acceptors) and the set (variety) of groups (R1)$_m$ containing of m elements comprises donors (R1') and/or acceptors (R1). The electrophilic groups (acceptors) are selected from —NO$_2$, —NH$_3$+ and —NR$_3$+(quaternary nitrogen salts), counterion Cl— or Br—, —CHO (aldehyde), —CRO (keto group), —SO$_3$H (sulfonic acids), —SO$_3$R (sulfonates), —SO$_2$NH$_2$ (sulfonamides), —COOH (carboxylic acid), —COOR (esters, from carboxylic acid side), —COCl (carboxylic acid chlorides), —CONH$_2$ (amides, from carboxylic acid side), —CF$_3$, —CCl$_3$, —CN, —C(CN)$_2$ wherein R is radical selected from the list comprising alkyl (methyl, ethyl, isopropyl, tert-butyl, neopentyl, cyclohexyl etc.), allyl (—CH$_2$—CH=CH$_2$), benzyl (—CH$_2$C$_6$H$_5$) groups, phenyl (+substituted phenyl) and other aryl (aromatic) groups. The nucleophilic groups (donors) are selected from —O— (phenoxides, like —ONa or —OK), —NH$_2$, —NHR, —NR$_2$, —OH, —OR (ethers), —NHCOR (amides, from amine side), —OCOR (esters, from alcohol side), alkyls, —C$_6$H$_5$, vinyls, wherein R is radical selected from the list comprising alkyl (methyl, ethyl, isopropyl, tert-butyl, neopentyl, cyclohexyl etc.), allyl (—CH$_2$—CH=CH$_2$), benzyl (—CH$_2$C$_6$H$_5$) groups, phenyl (+substituted phenyl) and other aryl (aromatic) groups.

In still another embodiment of the disclosed electropolarizable compound, at least one connecting group is selected from the list comprising the following structures: 13-23 given in Table 3, where X is hydrogen (H) or an alkyl group.

TABLE 3

Examples of the connecting group

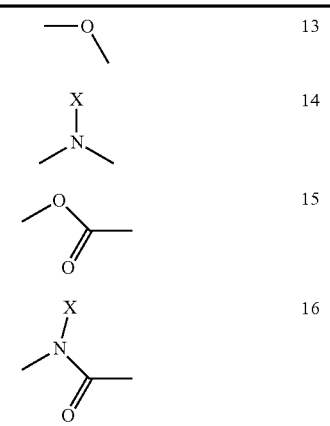

13

14

15

16

TABLE 3-continued

| Examples of the connecting group | |
|---|---|
| ![structure 17] | 17 |
| ![structure 19] | 19 |
| ![structure 20] | 20 |
| ![structure 21] | 21 |
| ![structure 22] | 22 |

In one embodiment of the present disclosure, the at least one connecting group is selected from the group of $CH_2$, $CF_2$, $SiR_2O$, $CH_2CH_2O$, wherein R is selected from the list comprising H, alkyl, and fluorine. In another embodiment of the present disclosure, the at least one connecting group is selected from structures 24 to 29 as given in Table 4.

TABLE 4

| Examples of the connecting group | |
|---|---|
| ![structure 24] | 24 |
| ![structure 25] | 25 |
| ![structure 26] | 26 |
| ![structure 27] | 27 |
| ![structure 28] | 28 |
| ![structure 29] | 29 |

In yet another embodiment of the present disclosure, the resistive substituent R4 is selected from the group of alkyl, aryl, substituted alkyl, substituted aryl, fluorinated alkyl, chlorinated alkyl, branched and complex alkyl, branched and complex fluorinated alkyl, branched and complex chlorinated alkyl groups, and any combination thereof, and wherein the alkyl group is selected from methyl, ethyl, propyl, n-butyl, iso-butyl and tert-butyl groups, and the aryl group is selected from phenyl, benzyl and naphthyl groups or siloxane, and/or polyethyleneglycol as linear or branched chains. In still another embodiment of the present disclosure, the resistive substituent R4 is $C_XQ_{2X+1}$, where $X \geq 1$ and Q is hydrogen (H), fluorine (F), or chlorine (Cl).

In one embodiment of the electro-polarizable compound, the aromatic polycyclic conjugated molecule (Core1) and the groups (R1) form a non-centrosymmetric molecular structure. In another embodiment of the electro-polarizable compound, the aromatic polycyclic conjugated molecule (Core1), the groups (R1) and the resistive substituents (R4) form a non-centrosymmetric molecular structure.

In one embodiment of the present disclosure, the electro-polarizable compound has the following general formula (II):

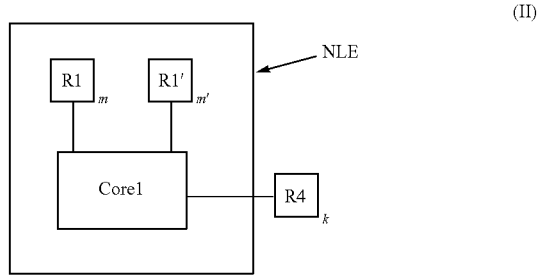

(II)

In general formula II, Core1 is the aromatic polycyclic conjugated molecule, as discussed above, the resistive substituent R4 is a non-conjugated part of disclosed compound, which may be saturated and fused cyclo-hydrocarbons or saturated and fused cyclo-halocarbons with rigid spatial structure including, but not limited to cyclohexane, cyclopentane, polycyclic perflourohexyls, polycyclic perflouropentyls, and structures that are built from tiles of cyclic carbon molecules. Wherein, the tiles of cyclic carbon molecules have dense packing of SP3 carbon saturated with H, F, Cl, Br. And, wherein parameters n=p=s=0. In another embodiment of the electro-polarizable compound, a length of the non-conjugated part is selected such that its resistivity is greater than $10^{18}$ ohm·cm. In yet another embodiment of the electro-polarizable compound, the resistive substituent R4 is a polycyclic alkyl group and a polycyclic halo-alkyl, wherein in the polycyclic halo-alkyl group is connected to the apex of Core1 on which the electrophilic group (acceptor) R1 is connected, or the apex of Core1 on which the nucleophilic group (donor) R1' is connected, but not both. In still another embodiment of the electro-polarizable compound, the resistive substituent R4 is resistive polycyclic substituents selected from the list comprising long $C_{25}H_{34}$ and $C_{25}H_{35}$ or $C_{25}F_{34}$ and $C_{25}F_{35}$ and located on the apex phenyl rings of Core1. In one embodiment of the present disclosure, the electro-polarizable compound has the following general formula (III):

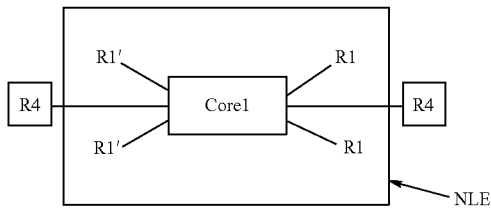
(III)

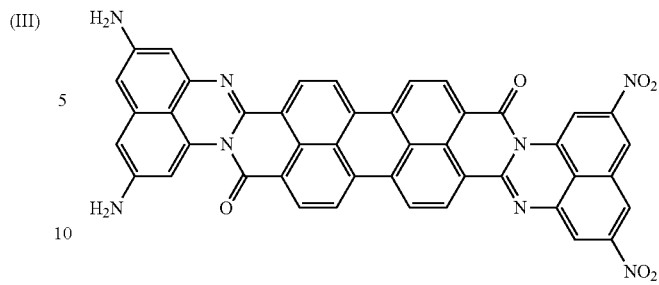

In general formula III, the parameter m is equal to 4, R1' is donor group, R1 is acceptor group, k is equal to 2. In another embodiment of the electro-polarizable compound, the Core1 is rylene fragment having following structural formula where repetition parameter t is an integer varying from 0 to 5:

wherein the resistive substituent (R4) is an amine structure of the following type:

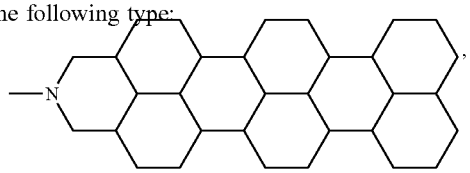

leading to the following structural formula (IV):

(IV)

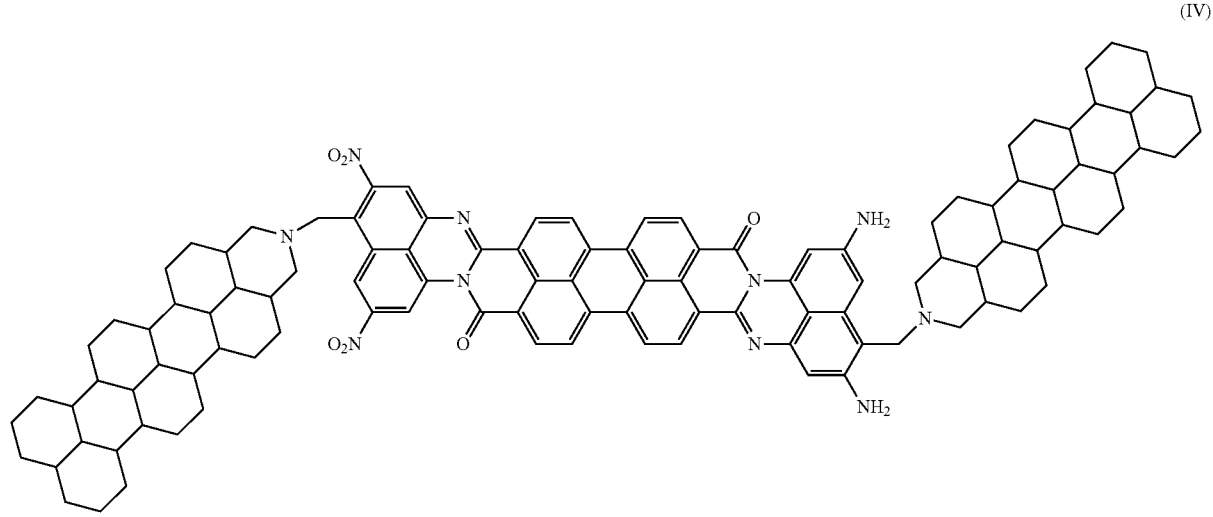 [SMILES: Nc1cc2c(CN3CC4CCC5C6CCC7C8CCCC9CCCC(C%10CCC(C%11CCC(C3)C4C5%11)C6C7%10)C98)c(N)cc3nc4c5ccc6c7ccc8c(=O)n9c%10cc([N+](=O)[O-])cc%11c(CN%12CC%13CCC%14C%15CCC%16C%17CCCC%18CCCC(C%19CCC(C%20CCC(C%12)C%13C%14%20)C%15C%16%19)C%18%17)c([N+](=O)[O-])cc(nc9c9ccc(c%12ccc(c(=O)n4c(c1)c32)c5c6%12)c7c89)c%11%10]

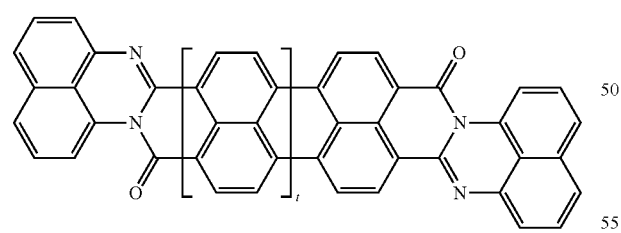

wherein the set of the electron donor and acceptor groups comprises two donor groups —NH$_2$ and two acceptor groups —NO$_2$ (m is equal to 4) located on rylene phenyl rings and/or apex phenyl ring positions of the Core1, so that the fragment having a nonlinear effect of polarization (NLE) is represented by the following chemical structure (when t=1):

wherein the resistive substituents are connected via a connecting group.

In another embodiment of the present disclosure, the electro-polarizable compound has the following general formula (V):

(V)

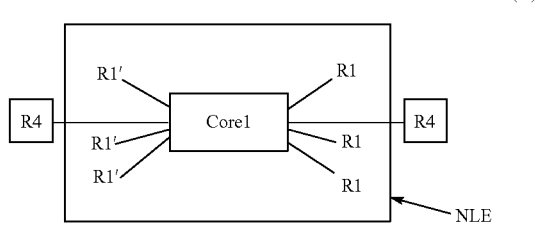

In general formula V, Core1 is the above-described aromatic polycyclic conjugated molecule, m is equal to 6, R1' is donor group, R1 is acceptor group, k is equal to 2. In yet another embodiment of the electro-polarizable compound, the Core1 is rylene fragment having following structural formula where repetition parameter t varies from 1 to 5:

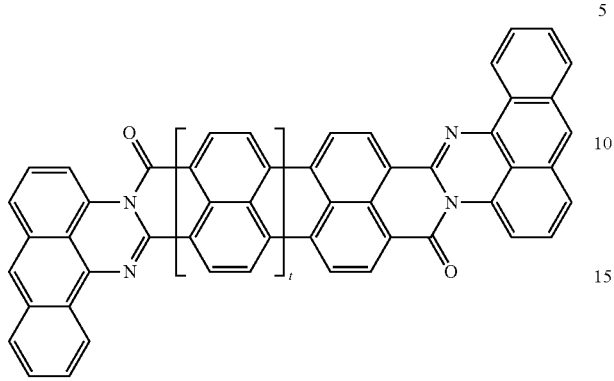

wherein the set of the electron donor and acceptor groups comprises three donor groups —NH$_2$ and three acceptor groups —NO$_2$ (m is equal to 6) are located on rylene phenyl rings and/or apex phenyl ring positions of the Core1, so that the fragment having a nonlinear effect of polarization (NLE) is represented by following chemical structure (when t=1):

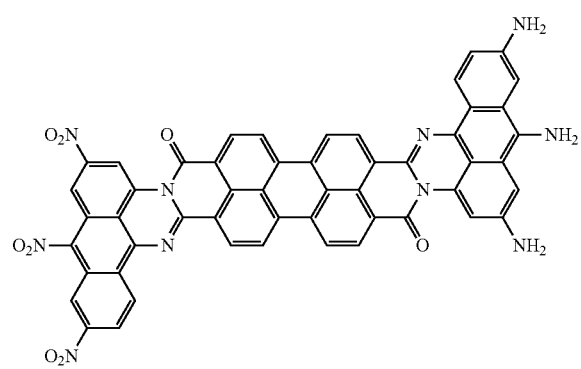 [SMILES: Nc1ccc2c(c1)c(N)c1cc(N)cc3c1c2nc1c2ccc4c5ccc6c(=O)n7c8cc([N+](=O)[O-])cc9c([N+](=O)[O-])c%10cc([N+](=O)[O-])ccc%10c(nc7c7ccc(c%10ccc(c(=O)n31)c2c4%10)c5c67)c98]

wherein the resistive substituent (R4) is an amine structure of the following type:

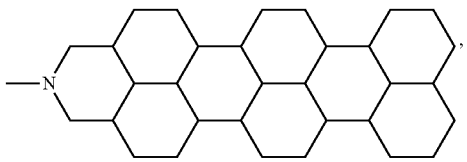

leading to the following structural formula (VI):

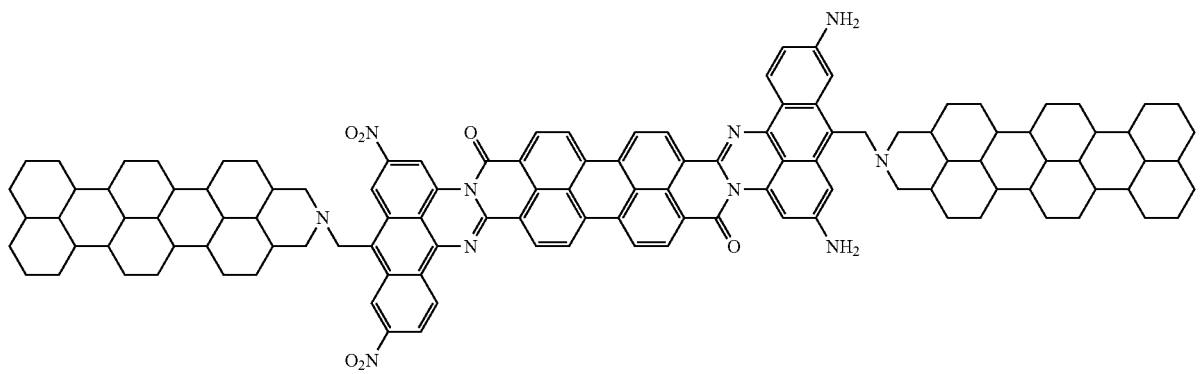 [SMILES: Nc1ccc2c(c1)c(CN1CC3CCC4C5CCC6C7CCCC8CCCC(C9CCC(C%10CCC(C1)C3C4%10)C5C69)C87)c1cc(N)cc3c1c2nc1c2ccc4c5ccc6c(=O)n7c8cc([N+](=O)[O-])cc9c(CN%10CC%11CCC%12C%13CCC%14C%15CCCC%16CCCC(C%17CCC(C%18CCC(C%10)C%11C%12%18)C%13C%14%17)C%16%15)c%10cc([N+](=O)[O-])ccc%10c(nc7c7ccc(c%10ccc(c(=O)n31)c2c4%10)c5c67)c98]

wherein the resistive substituents are connected via a connecting group.

In one embodiment of the present disclosure, the induced polarization $P_{ind}$ of the electro-polarizable compound may be written in the form of decomposition into a series on degrees of intensity of a local electric field $E_{loc}$:

$$P_{ind} = \alpha \cdot E_{loc} + \beta \cdot E_{loc}^2 + \ldots,$$

where $\alpha$ represents linear polarizability, $\beta$ represents square polarizability.

In an aspect, the present disclosure provides the organic solvent comprising the disclosed electro-polarizable compound. In one embodiment, the solution comprises a mixture of different electro-polarizable compounds. In another embodiment of the disclosed organic solvent, the mixture of the electro-polarizable compounds comprises the rylene fragments of different length. In still another embodiment, the organic solvent is selected from the list comprising ketones, carboxylic acids, hydrocarbons, cyclic hydrocarbons, chlorohydrocarbons, alcohols, ethers, esters, and any combination thereof. In yet another, the organic solvent is selected from the list comprising acetone, xylene, toluene, ethanol, methylcyclohexane, ethyl acetate, diethyl ether, octane, chloroform, methylene chloride, dichloroethane, trichloroethene, tetrachloroethene, carbon tetrachloride, 1,4-dioxane, tetrahydrofuran, pyridine, triethylamine, nitromethane, acetonitrile, dimethylformamide, dimethyl sulfoxide, and any combination thereof. In yet another embodiment of disclose, the solution is a lyotropic liquid crystal solution.

In another aspect, aspects of the present disclosure provide a crystal metadielectric layer comprising at least one type of the disclosed electro-polarizable compounds. The crystal metadielectric layers are produced from the disclosed organic compound by Cascade Crystallization; a method of thin crystal film (or thin crystal layer) manufacturing known as the Optiva-Process. See U.S. Pat. Nos. 5,739,296 and 6,049,428, and P. Lazarev et al., "X-ray Diffraction by Large Area Organic Crystalline Nano-films", Molecular Materials, 14 (4), 303-311 (2001), and Bobrov, "Spectral Properties of Thin Crystal Film Polarizers", Molecular Materials, 14 (3), 191-203 (2001).

Cascade Crystallization process involves a chemical modification step and four steps of ordering during the crystal metadielectric layer formation. The chemical modification step introduces hydrophilic groups on the periphery of the molecule of the disclosed organic compound in order to impart amphiphilic properties to the molecule. Amphiphilic molecules stack together into supramolecules, which is the first step of ordering. At certain concentration, supramolecules are converted into a liquid-crystalline state to form a lyotropic liquid crystal, which is the second step of ordering. The lyotropic liquid crystal is deposited under the action of a shear force (or meniscus force) onto a substrate based on a Mayer Rod shearing technique, so that shear force (or the meniscus) direction determines the crystal axis direction in the resulting solid crystal layer. The external alignment upon the lyotropic liquid crystal can be produced using any other means, for example by applying an external electric field at normal or elevated temperature, with or without additional illumination, magnetic field, or optical field (e.g., coherent photovoltaic effect); the degree of the external alignment should be sufficient to impart necessary orientation to the supramolecules of the lyotropic liquid crystal and form a structure, which serves as a base of the crystal lattice of the dielectric layer. This directional deposition is third step of ordering, representing the global ordering of the crystalline or polycrystalline structure on the substrate surface. The last fourth step of the Cascade Crystallization process is drying/crystallization, which converts the lyotropic liquid crystal into a solid crystal dielectric layer. The term Cascade Crystallization process is used to refer to the chemical modification and four ordering steps as a combination process.

The Cascade Crystallization process is used for production of thin crystalline metadielectric layers. The dielectric layer produced by the Cascade Crystallization process has a global order which means that direction of the crystallographic axis of the layer over the entire substrate surface is controlled by the deposition process. Molecules of the deposited material are packed into supramolecules with a limited freedom of diffusion or motion. The thin crystalline dielectric layer is characterized by an interplanar spacing of 3.4±0.3 Ångströms (Å) in the direction of one of the optical axes.

In one embodiment of the present disclosure, the crystal metadielectric layer comprises the column-like supramolecules formed by the electro-polarizable compounds comprising the rylene fragments of different length. The variety of the rylene fragment lengths increases the randomness of the stack. In one embodiment according to aspects of the present disclosure, the layer's relative permittivity is greater than or equal to 1000. In one embodiment, the real part of the relative permittivity ($\varepsilon'$) of the crystal metadielectric layer comprises first-order ($\varepsilon^{(1)}$) and second-order ($\varepsilon^{(2)}$) permittivities according to follow formula:

$$\varepsilon' = \varepsilon^{(1)} + 2\varepsilon^{(2)} \frac{V_0}{d},$$

where $V_0$ is the DC-voltage which is applied to the crystal metadielectric layer, d is the layer thickness. In another embodiment of the present invention, the layer's resistivity is greater than or equal to $10^{13}$ ohm/cm.

The present disclosure provides the metacapacitor comprising two metal electrodes positioned parallel to each other and which can be rolled or flat and planar and metadielectric layer between said electrodes. The layer comprises the electro-polarizable compounds as disclosed above.

The metacapacitor comprises a first electrode 1, a second electrode 2, and a metadielectric layer 3 disposed between said first and second electrodes as shown in FIG. 1A. The electrodes 1 and 2 may be made of a metal, such as copper, zinc, or aluminum or other conductive material such as graphite or carbon nanomaterials and are generally planar in shape.

The electrodes 1, 2 may be flat and planar and positioned parallel to each other. Alternatively, the electrodes may be planar and parallel, but not necessarily flat, they may be coiled, rolled, bent, folded, or otherwise shaped to reduce the overall form factor of the capacitor. It is also possible for the electrodes to be non-flat, non-planar, or non-parallel or some combination of two or more of these. By way of example and not by way of limitation, a spacing d between the electrodes l and 2 may range from about 100 nm to about 10 000 μm. The maximum voltage $V_{bd}$ between the electrodes 1 and 2 is approximately the product of the breakdown field $E_{bd}$ and the electrode spacing d. If $E_{bd}$=0.1 V/nm and the spacing d between the electrodes 1 and 2 is 10,000 microns (100,000 nm), the maximum voltage $V_{bd}$ would be 100,000 volts.

The electrodes 1 and 2 may have the same shape as each other, the same dimensions, and the same area A. By way of example, and not by way of limitation, the area A of each electrode 1 and 2 may range from about 0.01 m² to about 1000 m². By way of example and not by way of limitation for rolled capacitors, electrodes up to, e.g., 1000 m long and 1 m wide.

These ranges are non-limiting. Other ranges of the electrode spacing d and area A are within the scope of the aspects of the present disclosure.

If the spacing d is small compared to the characteristic linear dimensions of electrodes (e.g., length and/or width), the capacitance C of the capacitor may be approximated by the formula:

$$C=\varepsilon\varepsilon_o A/d, \qquad (V)$$

where $\varepsilon_o$ is the permittivity of free space (8.85×10⁻¹² Coulombs²/(Newton·meter²)) and c is the dielectric constant of the dielectric layer. The energy storage capacity U of the capacitor may be approximated as:

$$U=\tfrac{1}{2}\varepsilon\varepsilon_o A E_{bd}^2 \qquad (VI)$$

The energy storage capacity U is determined by the dielectric constant $\varepsilon$, the area A, and the breakdown field $E_{bd}$. By appropriate engineering, a capacitor or capacitor bank may be designed to have any desired energy storage capacity U. By way of example, and not by way of limitation, given the above ranges for the dielectric constant $\varepsilon$, electrode area A, and breakdown field $E_{bd}$ a capacitor in accordance with aspects of the present disclosure may have an energy storage capacity U ranging from about 500 Joules to about $2 \cdot 10^{16}$ Joules.

For a dielectric constant c ranging, e.g., from about 100 to about 1,000,000 and constant breakdown field $E_{bd}$ between, e.g., about 0.1 and 0.5 V/nm, a capacitor of the type described herein may have a specific energy capacity per unit mass ranging from about 10 W·h/kg up to about 100,000 W·h/kg, though implementations are not so limited.

Figure 1B:
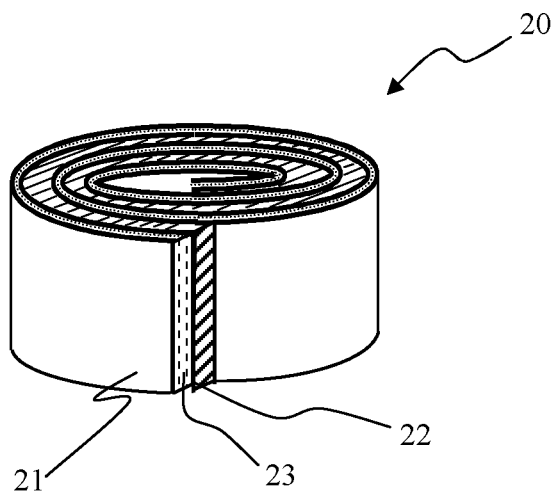
FIG. 1B schematically shows a capacitor with rolled (circular) electrodes in accordance with another aspect of the present disclosure.

The present disclosure includes metacapacitors that are coiled, e.g., as depicted in FIG. 1B. In this example, a metacapacitor 20 comprises a first electrode 21, a second electrode 22, and a metadielectric material layer 23 of the type described hereinabove disposed between said first and second electrodes. The electrodes 21 and 22 may be made of a metal, such as copper, zinc, or aluminum or other conductive material such as graphite or carbon nanomaterials and are generally planar in shape. In one implementation, the electrodes and metadielectric material layer 23 are in the form of long strips of material that are sandwiched together and wound into a coil along with an insulating material, e.g., a plastic film such as polypropylene or polyester to prevent electrical shorting between the electrodes 21 and 22.

In order that the invention may be more readily understood, reference is made to the following examples, which are intended to be illustrative of the invention, but are not intended to limit its scope.

Example 1

This Example describes synthesis of the disclosed organic compound according following structural scheme:

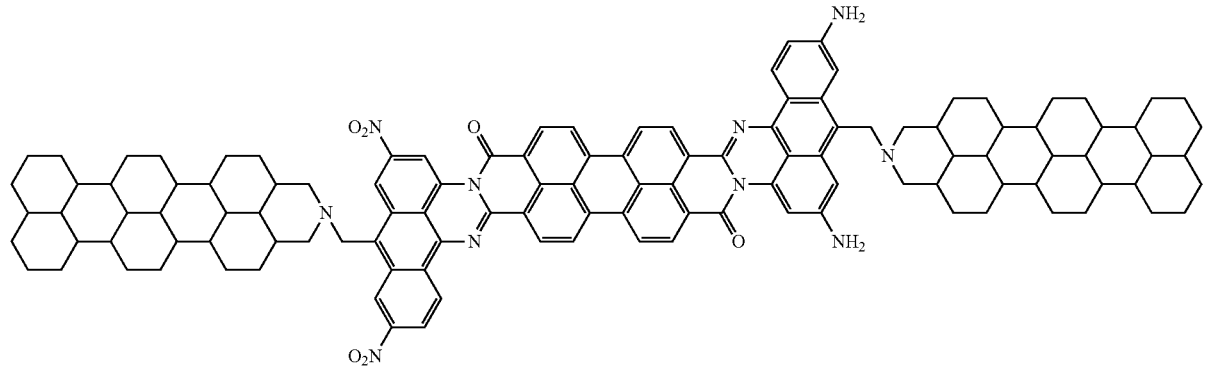

Procedure

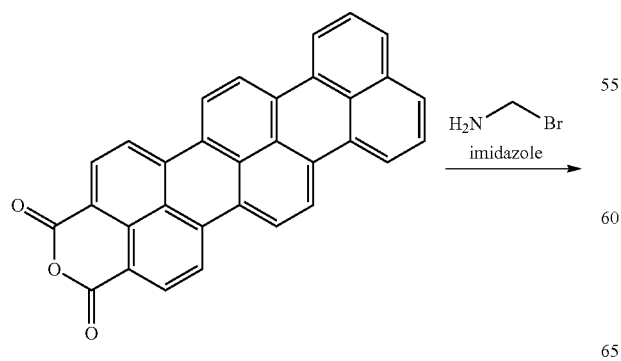

-continued

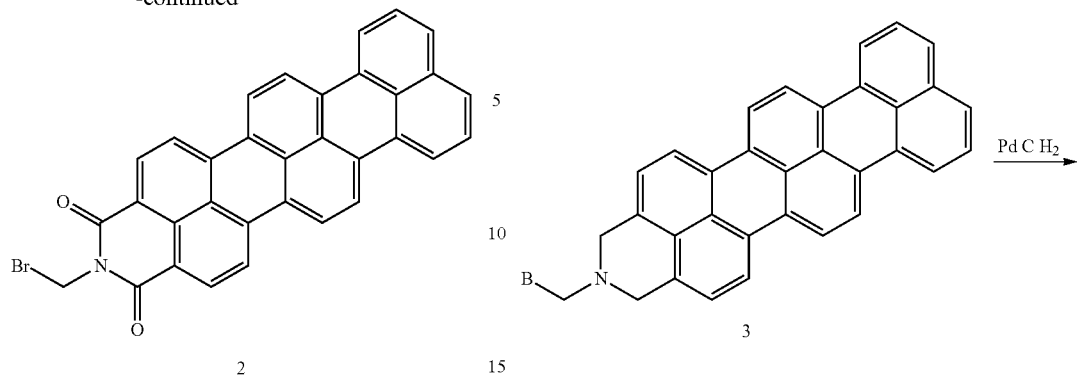

Terrylene anhydride 1 (1 equiv.) and 1-bromomethanamine (1 equiv.) were stirred in imidazole at 130° C. overnight. The mixture was dissolved in THF and washed with water 3 times. The organics were combined and dried over MgSO$_4$. The solvent was removed under reduced pressure to give 2.

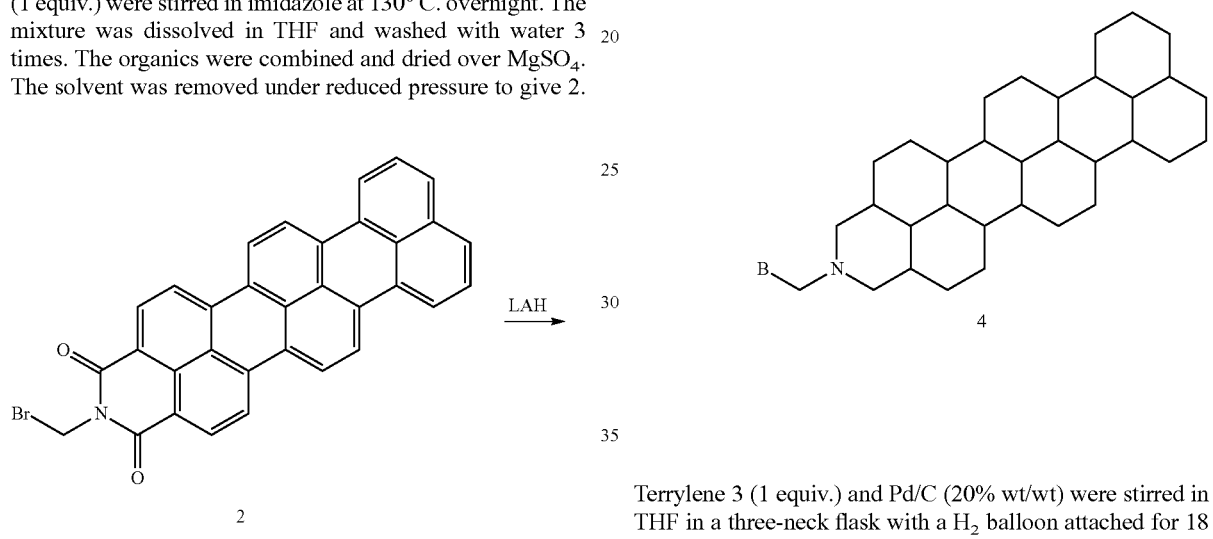

Terrylene imide 2 (1 equiv.) was dissolved in THF and stirred over an ice bath. Lithium aluminum hydride (5 equiv.) dissolved in THF was slowly added. The mixture was allowed to warm to ambient temperature and stirred for 18 h. The mixture was quenched with 2M NaOH, filtered, and dried over MgSO$_4$, and the solvent was removed under reduced pressure to give 3.

Terrylene 3 (1 equiv.) and Pd/C (20% wt/wt) were stirred in THF in a three-neck flask with a H$_2$ balloon attached for 18 h. The mixture was filtered through Celite and the solvents were removed under reduced pressure to give 4.

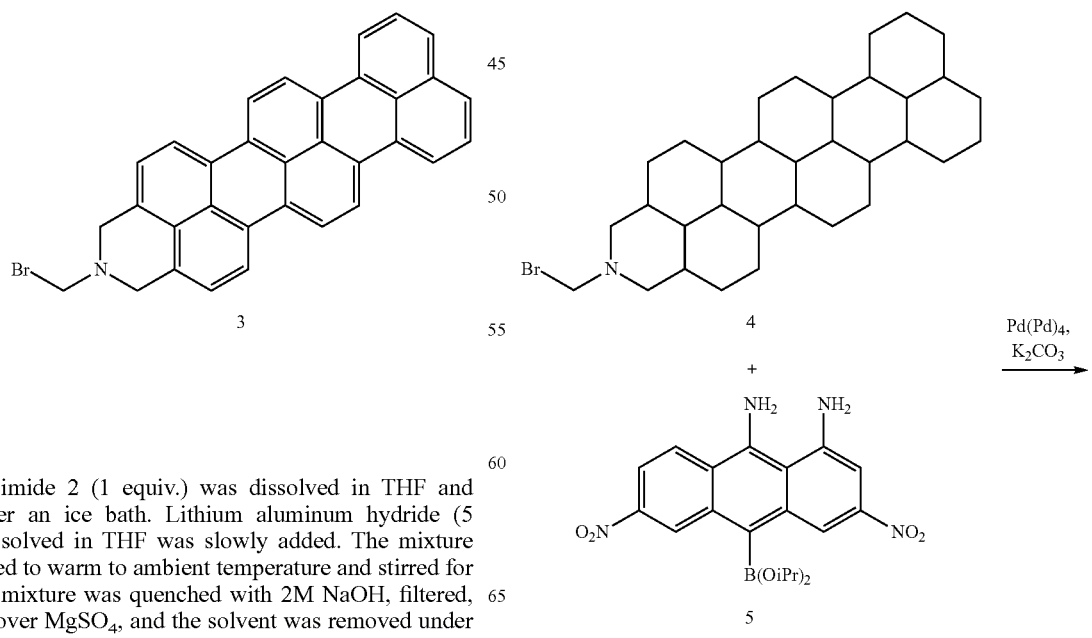

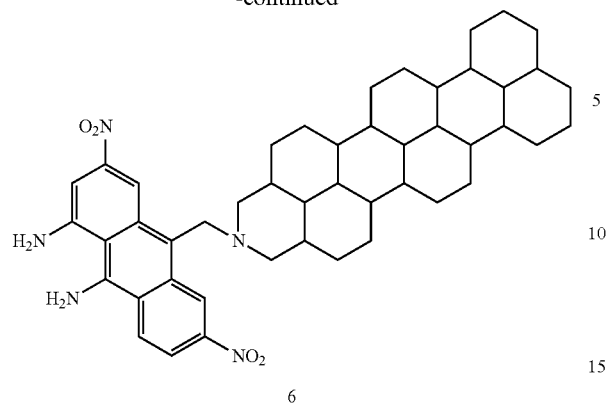
6
Bromo-amine 4 (1 equiv.), Anthracene 5 (1 equiv.), Pd(Ph)$_4$ (10 mol %), K$_2$CO$_3$ (1.5 equiv.) were stirred in toluene at 70° C. for 18 h. The mixture was filtered through Celite and the filtrate was washed with NaHCO$_3$ and brine. The organics were dried over MgSO$_4$, and the solvents were removed under reduced pressure to give 6.
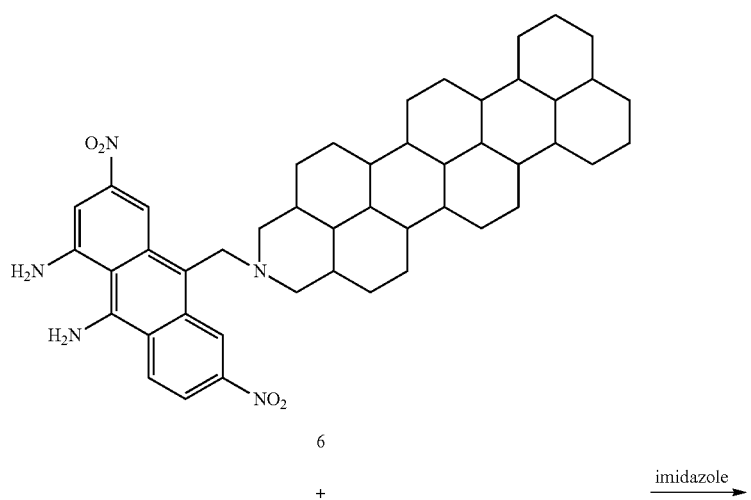
6
+
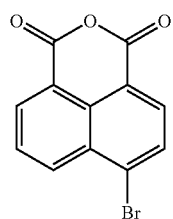
7
$\xrightarrow{\text{imidazole}}$

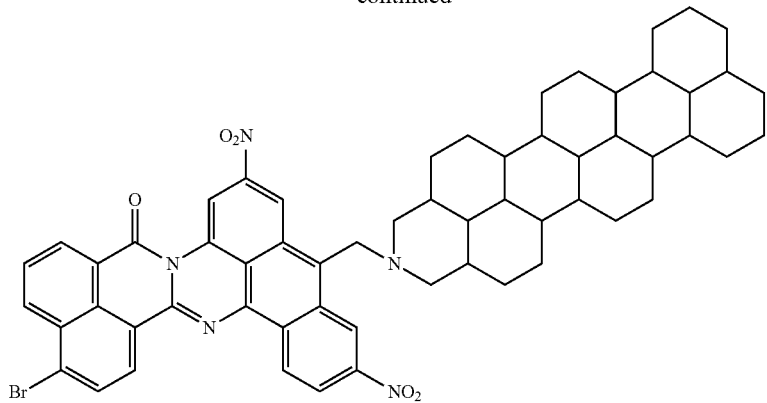

8

Naphthalene anhydride 7 (1 equiv.) and anthracene 6 (1 equiv.) were stirred in imidazole at 130° C. overnight. The mixture was dissolved in THF and washed with water 3 times. The organics were combined and dried over $MgSO_4$. The solvent was removed under reduced pressure to give 8.

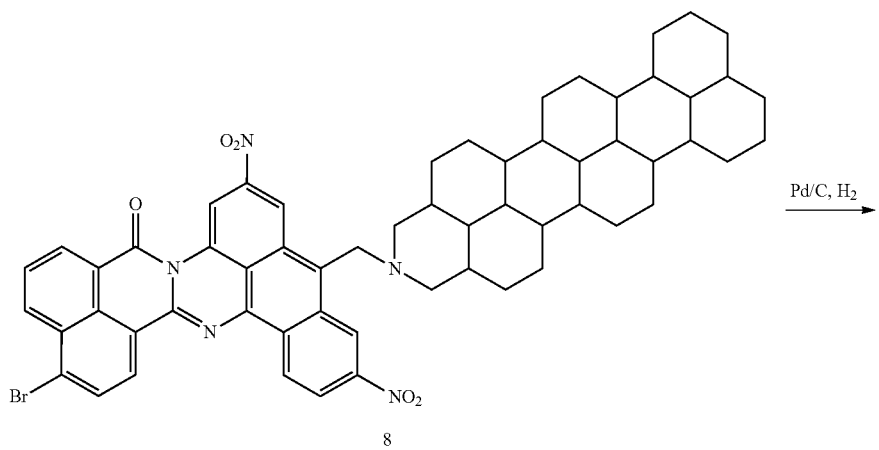

8

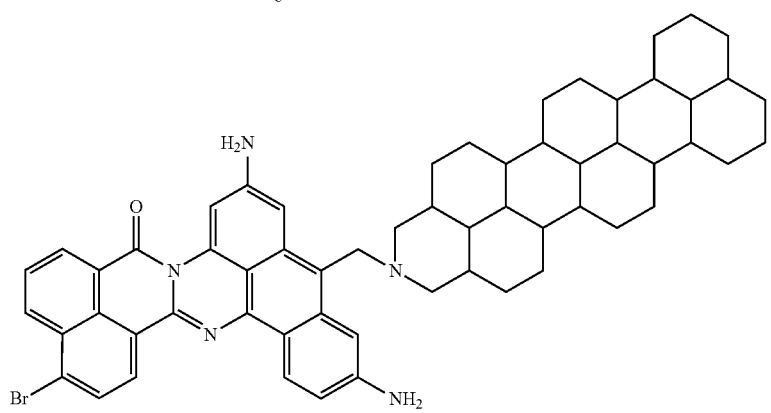

9

Amidine 8 (1 equiv.) and Pd/C (20% wt/wt) were stirred in THF in a three-neck flask with a $H_2$ balloon attached for 18 h. The mixture was filtered through Celite and the solvents were removed under reduced pressure to give 9.

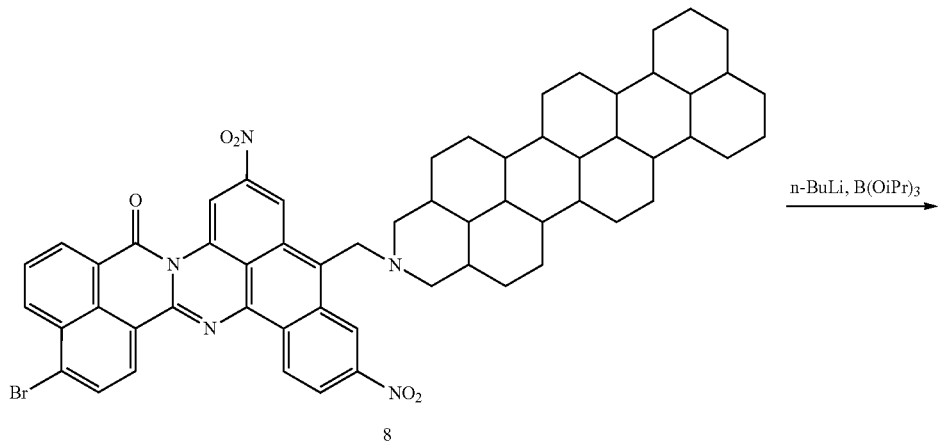
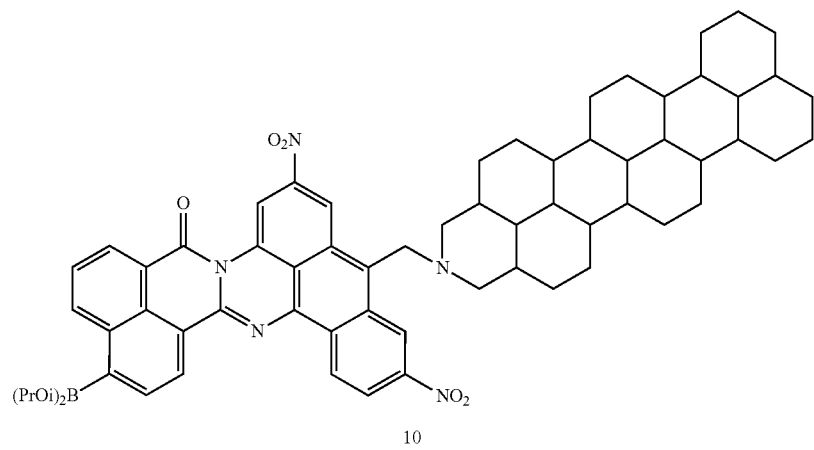
Amidine 8 (1 equiv.) was dissolved in THF and stirred at −80° C. N-butyllithium (1.2 equiv., 2.5 M in hexanes) was added dropwise. After 1 h, triisopropylborane was added dropwise and allowed to warm to room temperature overnight. The mixture was washed with NaHCO$_3$ and brine and dried over MgSO$_4$. The solvent was removed under reduced pressure to give 10.
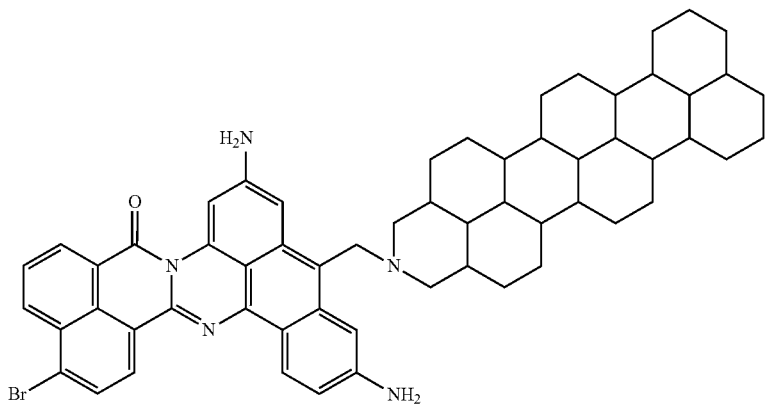

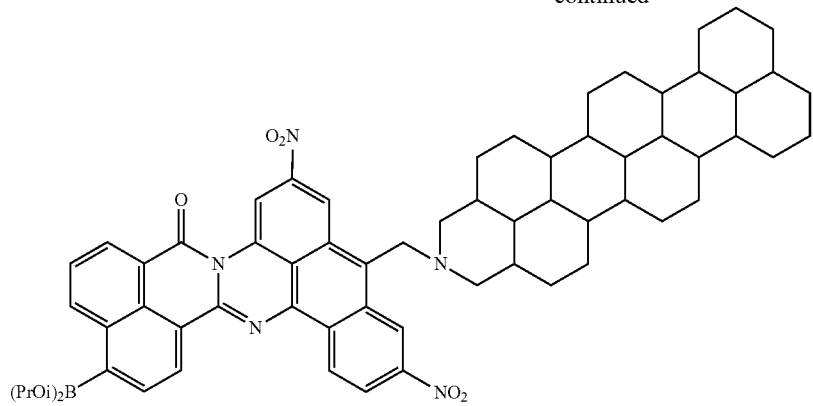
10
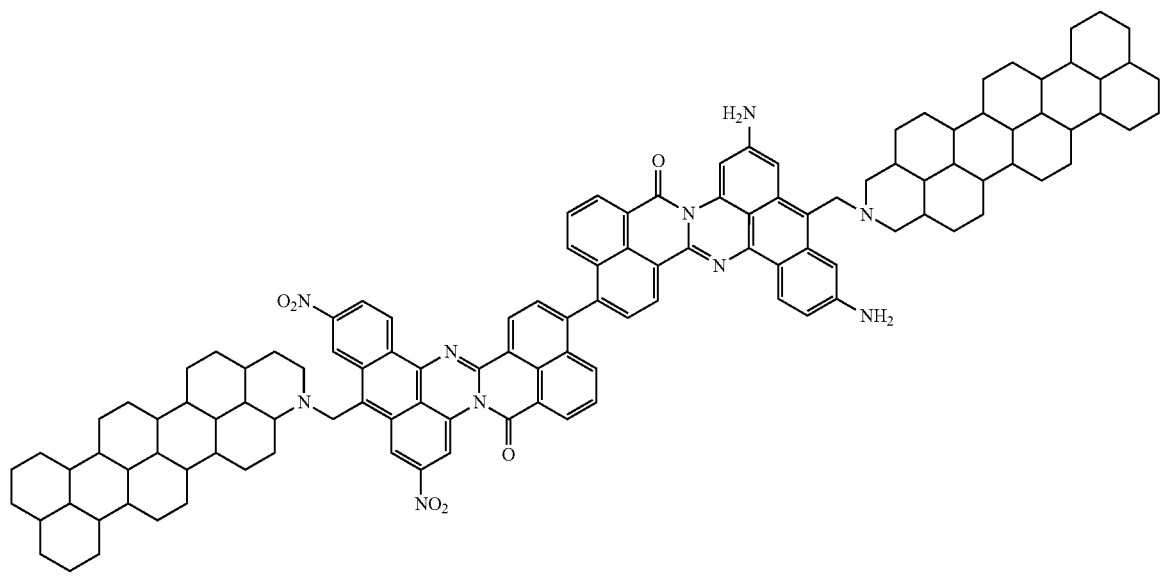
11
Bromo-amidine 9 (1 equiv.), Amidine boronic ester 10 (1 equiv.), Pd(Ph)$_4$ (10 mol %), K$_2$CO$_3$ (1.5 equiv.) were stirred in toluene at 70° C. for 18 h. The mixture was filtered through Celite and the filtrate was washed with NaHCO$_3$ and brine. The organics were dried over MgSO$_4$, and the solvents were removed under reduced pressure to give 11.

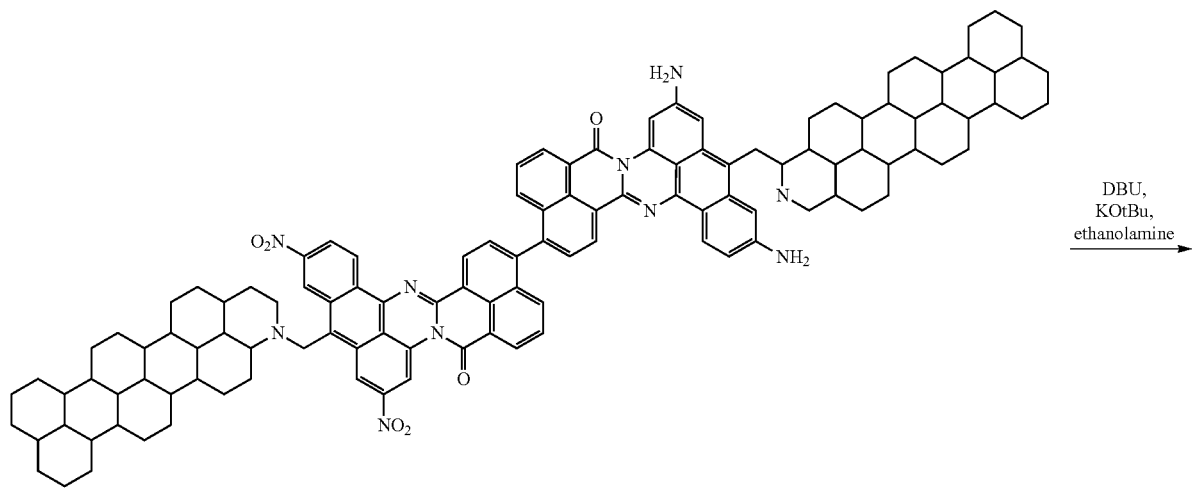

11

DBU,
KOtBu,
ethanolamine
→

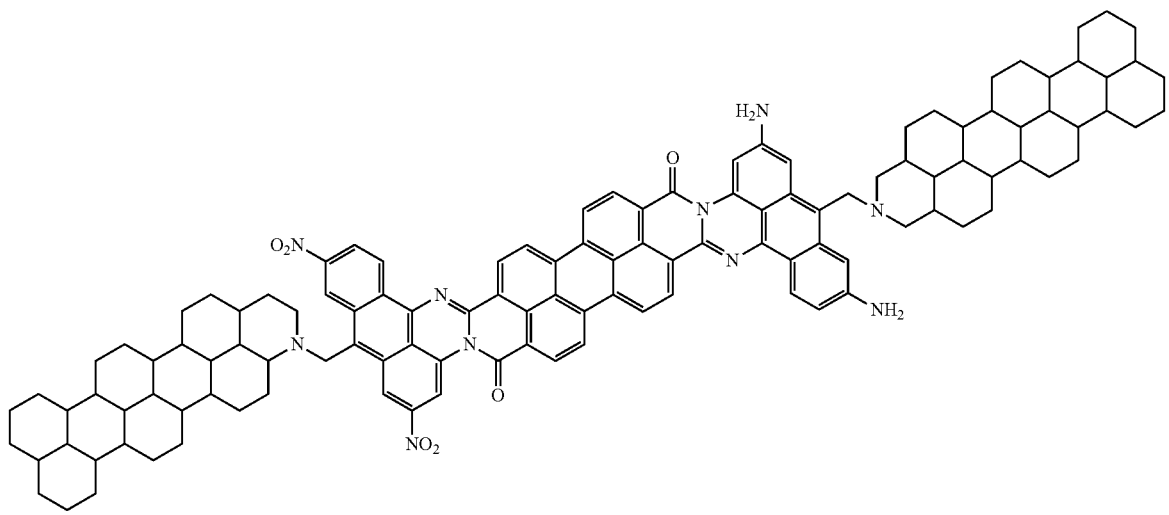

12

A mixture of 1.48 g (13 mmol) potassium tert-butoxide 2.30 g (15.1 mmol) of diazabicyclo[5.4.0]undec-7-ene (DBU), 2.2 g 36.3 mmol) ethanolamine and 1.0 g of 11 was heated to 140° C. for 11 hours. Afterwards, the same amount of potassium tert-butoxide, DBU and ethanolamine were added and the mixture was kept at 140° C. for 18 hours. The reaction mixture was cooled to room temperature, poured into 250 ml of 1M HCl filtered, washed until neutral pH and then dried to give the final product 12.

Example 2
This Example describes synthesis of the disclosed organic compound according following structural scheme:
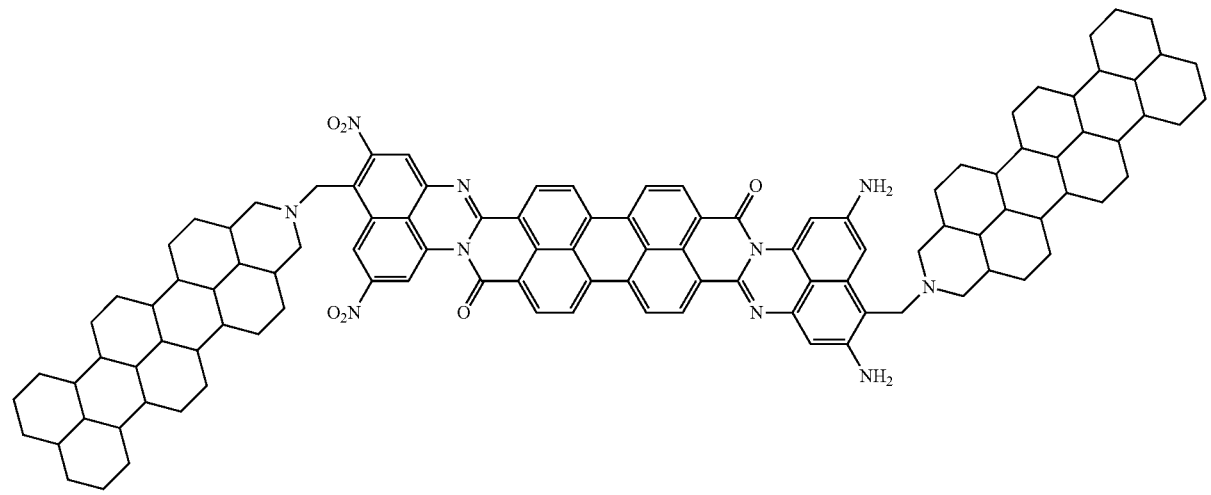 [SMILES: Nc1cc2c(CN3CC4CCC5C6CCC7C8CCCC9CCCC(C%10CCC(C%11CCC(C3)C4C5%11)C6C7%10)C98)c(N)cc3nc4c5ccc6c7ccc8c(=O)n9c%10cc([N+](=O)[O-])cc%11c(CN%12CC%13CCC%14C%15CCC%16C%17CCCC%18CCCC(C%19CCC(C%20CCC(C%12)C%13C%14%20)C%15C%16%19)C%18%17)c([N+](=O)[O-])cc(nc9c9ccc(c%12ccc(c(=O)n4c(c1)c32)c5c6%12)c7c89)c%11%10]
Procedure
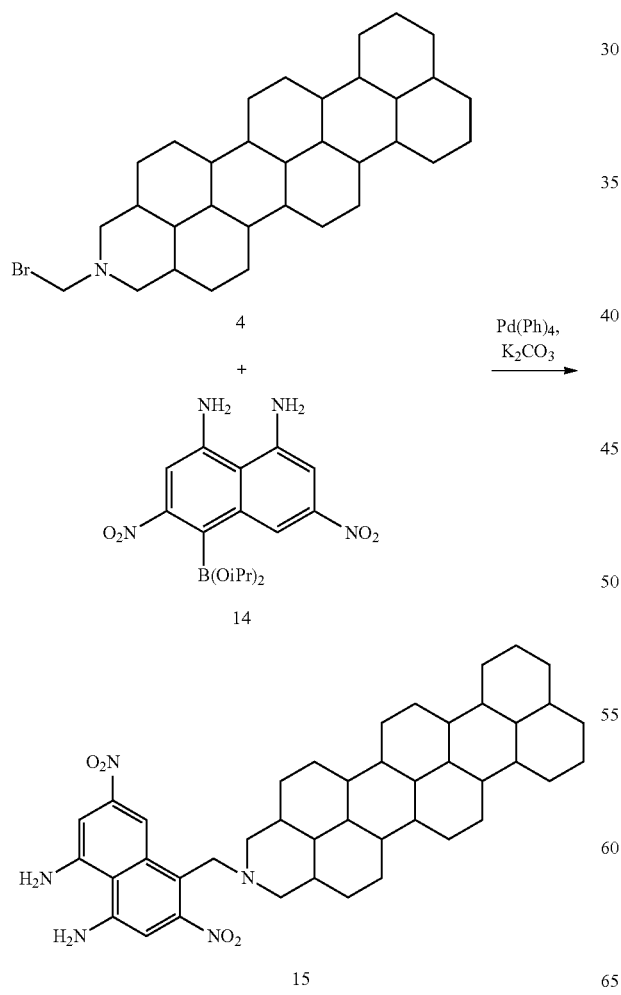

Bromo-amine 4 (1 equiv.), Naphthalene 14 (1 equiv.), Pd(Ph)$_4$ (10 mol %), K$_2$CO$_3$ (1.5 equiv.) were stirred in toluene at 70° C. for 18 h. The mixture was filtered through Celite and the filtrate was washed with NaHCO$_3$ and brine. The organics were dried over MgSO$_4$, and the solvents were removed under reduced pressure to give 15.

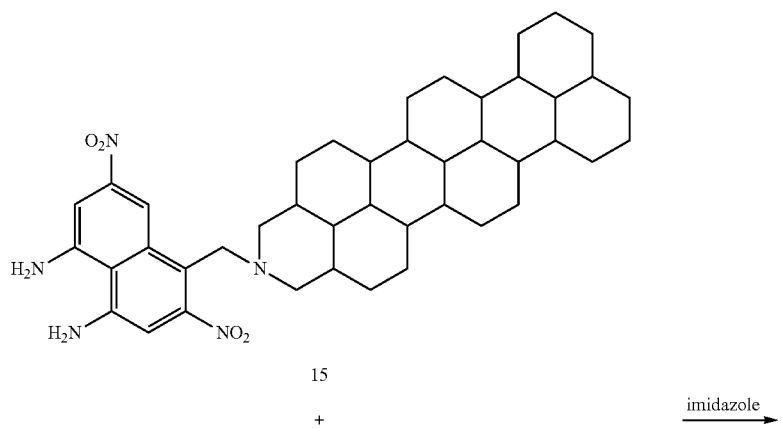

15

+

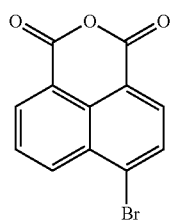

16 imidazole →

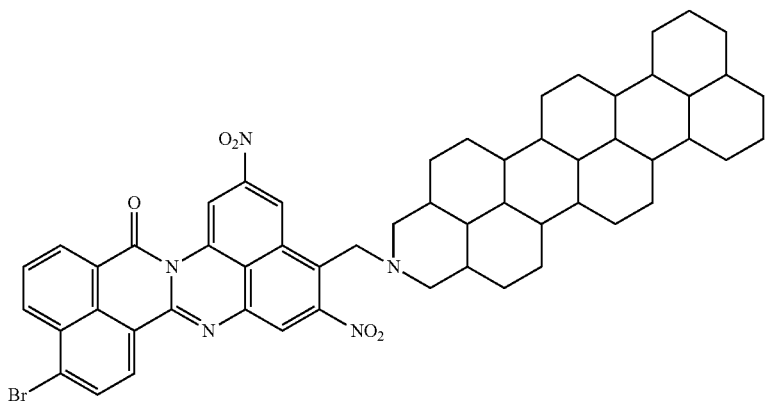

17

Naphthalene anhydride 16 (1 equiv.) and naphthalene 15 (1 equiv.) were stirred in imidazole at 130° C. overnight. The mixture was dissolved in THF and washed with water 3 times. The organics were combined and dried over MgSO$_4$. The solvent was removed under reduced pressure to give 17.

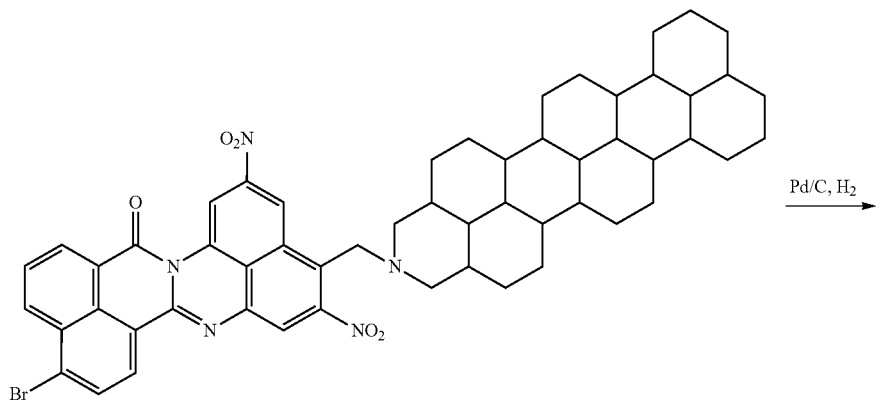
17
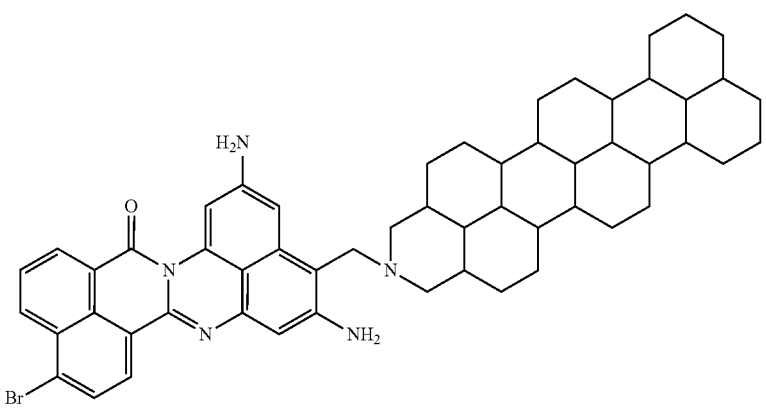
18
Amidine 17 (1 equiv.) and Pd/C (20% wt/wt) were stirred in THF in a three-neck flask with a $H_2$ balloon attached for 18 h. The mixture was filtered through Celite and the solvents were removed under reduced pressure to give 18.
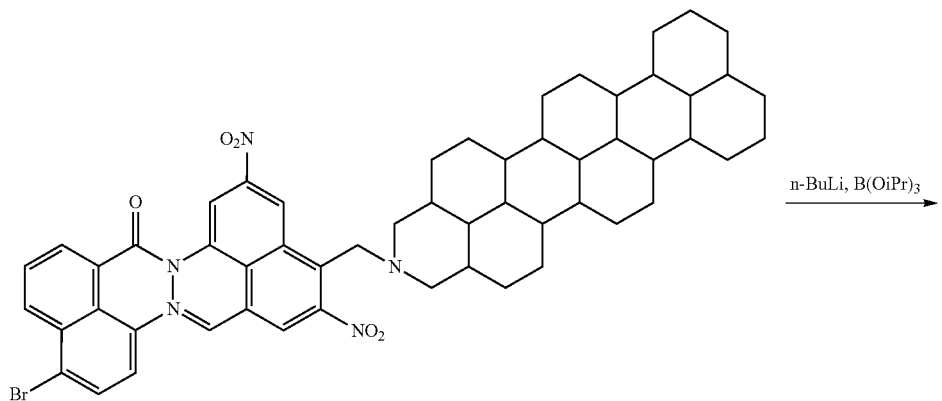
17

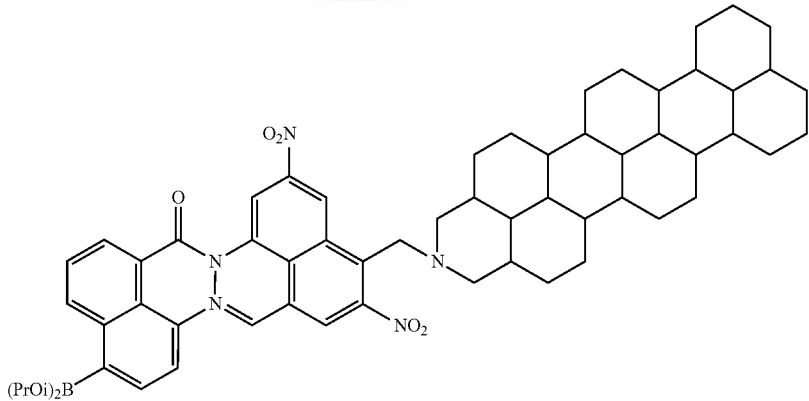
19
Amidine 17 (1 equiv.) was dissolved in THF and stirred at −80° C. N-butyllithium (1.2 equiv., 2.5 M in hexanes) was added dropwise. After 1 h, triisopropylborane was added dropwise and allow to warm to room temperature overnight. The mixture was washed with NaHCO$_3$ and brine and dried over MgSO$_4$. The solvent was removed under reduced pressure to give 19.
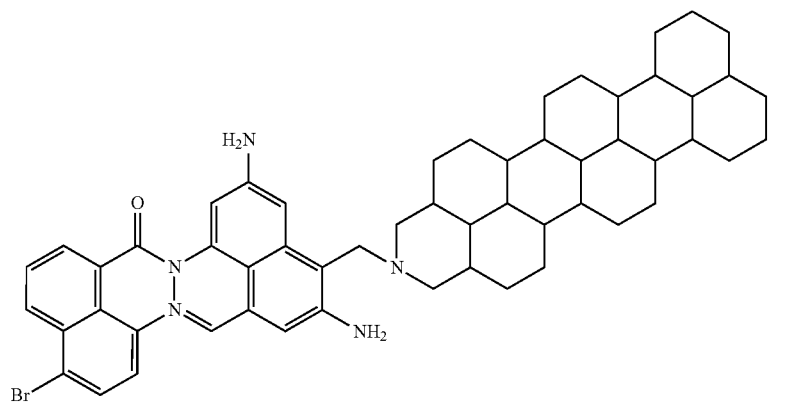
18
Pd(Ph$_4$), K$_2$CO$_3$
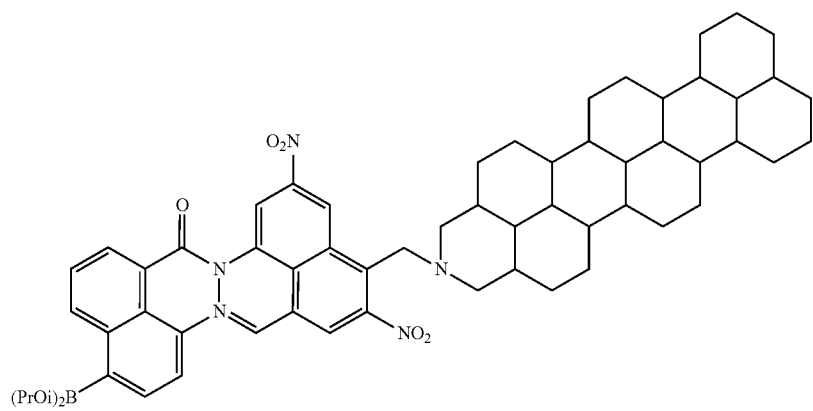
19

-continued
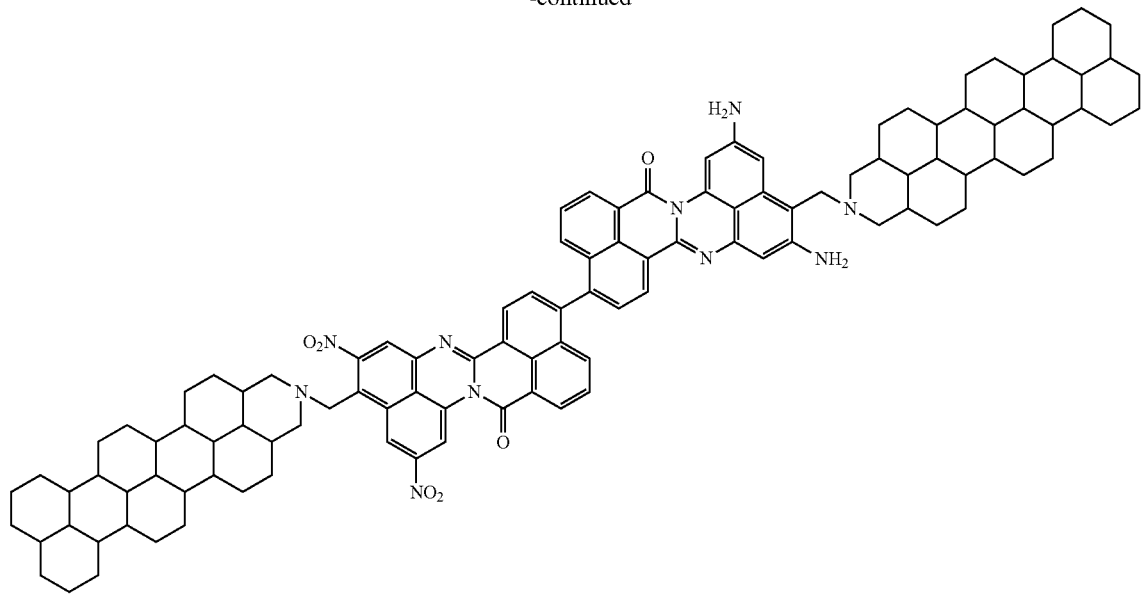
20
Bromo-amidine 18 (1 equiv.), Amidine boronic ester 19 (1 equiv.), Pd(Ph)$_4$ (10 mol %), K$_2$CO$_3$ (1.5 equiv.) were stirred in toluene at 70° C. for 18 h. The mixture was filtered through Celite and the filtrate was washed with NaHCO$_3$ and brine. The organics were dried over MgSO$_4$, and the solvents were removed under reduced pressure to give 20.
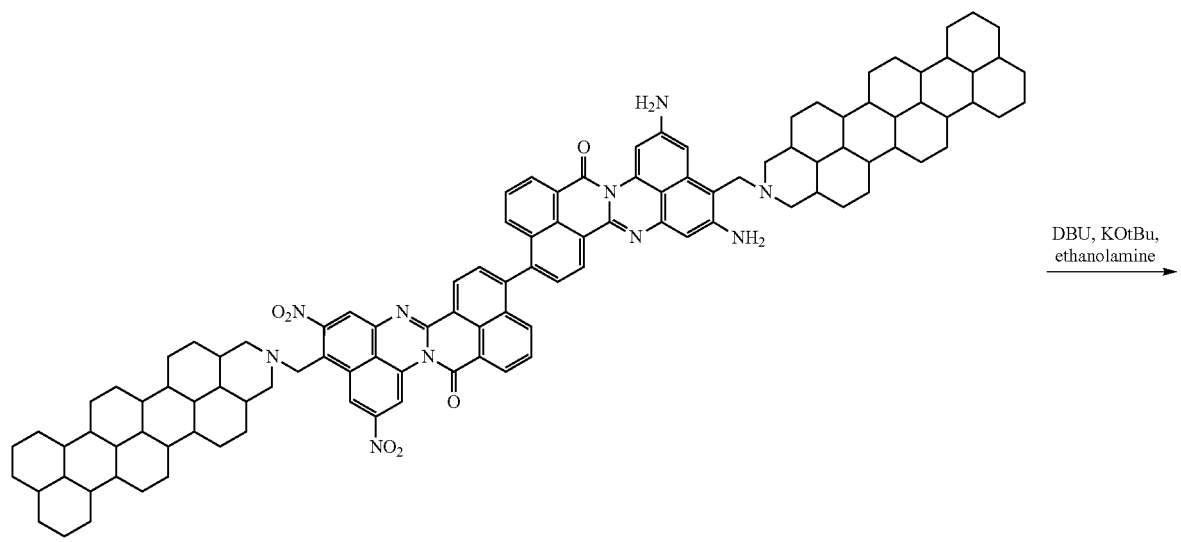
20
DBU, KOtBu, ethanolamine
→

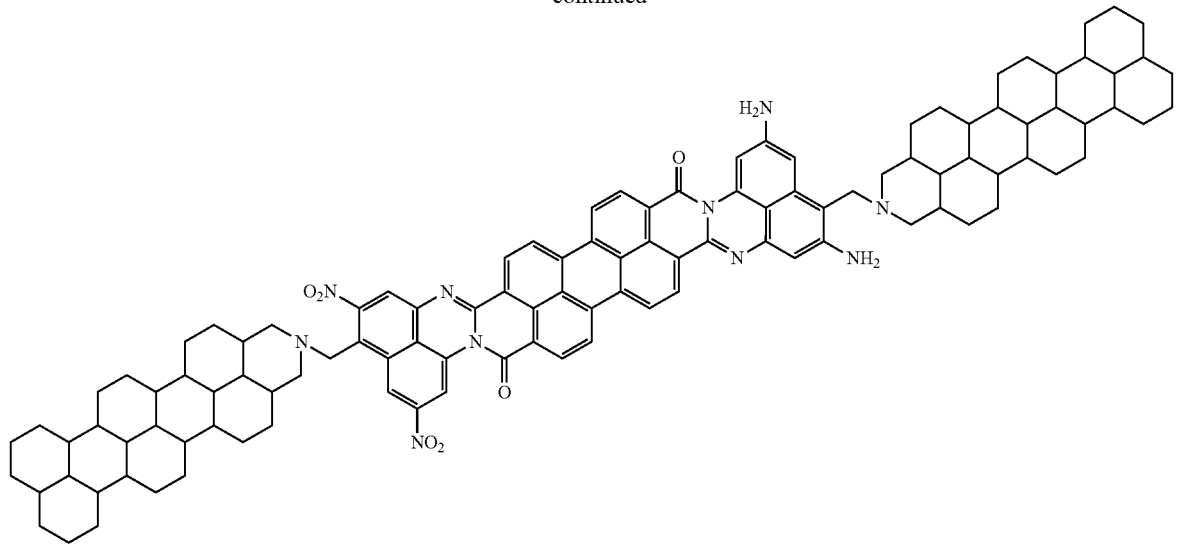

21

A mixture of 1.48 g (13 mmol) potassium tert-butoxide 2.30 g (15.1 mmol) of diazabicyclo[5.4.0]undec-7-ene (DBU), 2.2 g 36.3 mmol) ethanolamine and 1.0 g of 20 was heated to 140° C. for 11 hours. Afterwards, the same amount of potassium tert-butoxide, DBU and ethanolamine were added and the mixture was kept at 140° C. for 18 hours. The reaction mixture was cooled to room temperature, poured into 250 ml of 1M HCl filtered, washed until neutral pH and then dried to give the final product 21.

Aspects of the present disclosure provide compounds characterized by highly nonlinear electric polarizabilitly. Such compounds are useful as high dielectric constant metadielectrics for metacapacitors with extremely high capacitance and extremely high energy storage capacity. While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. As used herein, in a listing of elements in the alternative, the word "or" is used in the logical inclusive sense, e.g., "X or Y" covers X alone, Y alone, or both X and Y together, except where expressly stated otherwise. Two or more elements listed as alternatives may be combined together. The appended claims are not to be interpreted as including means-plus-function limitations, unless such a limitation is explicitly recited in a given claim using the phrase "means for."

What is claimed is:

1. An electro-polarizable compound having the following formula (I):

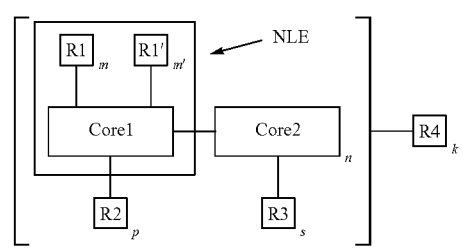

wherein the Core1 is selected from the following structures:

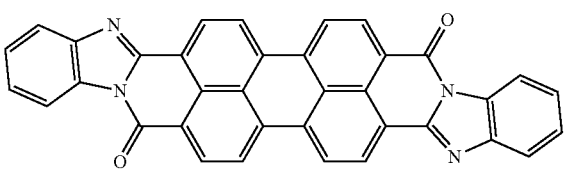

1

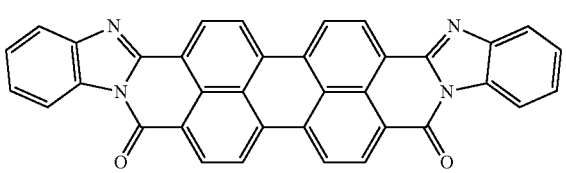

2

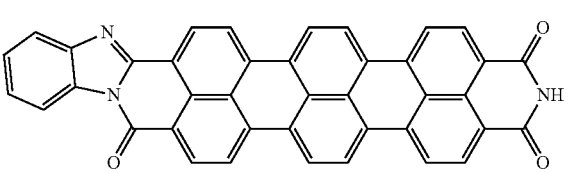

4

-continued

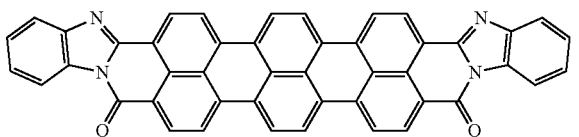

7

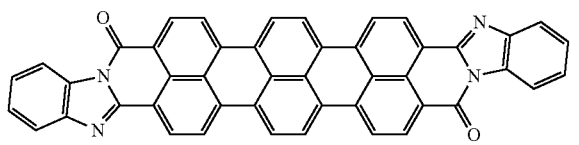

8

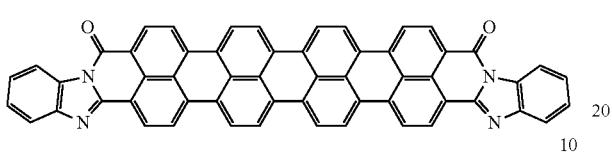

9

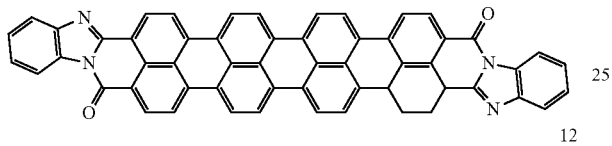

10

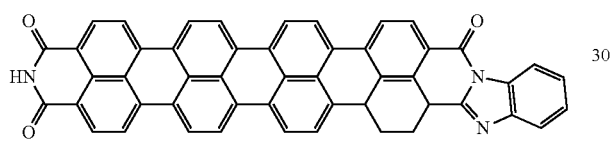

12

R1 is an electron donor group connected to Core1 and R1' is an electron acceptor group connected to the Core1, m is number of acceptor group R1, m' is a number of donor group R', m and m' are equal to 0, 1, 2, 3, 4, 5 or 6, wherein m and m' are not both equal to 0, R2 is a substituent comprising one or more ionic groups from a class of ionic compounds that form ionic liquids connected to the Core1 directly or via a connecting group, p is a number of ionic groups R2 which is equal to 0, 1, 2, 3 or 4;

wherein the fragment marked NLE containing the Core1 with at least one group R1 and/or R1' has a nonlinear effect of polarization, wherein Core2 is an electro-conductive oligomer, n is a number equal to 0, 2, or 4, R3 is a substituent comprising one or more ionic groups from a class of ionic compounds that form ionic liquids connected to the Core2 directly or via a connecting group, s is a number of the ionic groups R3 which is equal to 0, 1, 2, 3 or 4;

wherein R4 is a non-conjugate cyclic or polycyclic resistive substituent electrically insulating the column-like supramolecules from each other and connected to the aromatic polycyclic conjugated molecule (Core1) and/or to the Core2 directly or via a connecting group, k is a number of substituents R4 which is equal to 1, 2, 3, 4, 5, 6, 7 or 8.

2. The electro-polarizable compound according to claim 1, wherein the acceptor groups (R1') are selected from —NO$_2$, —NH$_3^+$, —NR$_3^+$, Cl$^-$, Br$^-$, —CHO, —CRO, —SO$_3$H, —SO$_3$R, —SO$_2$NH$_2$, —COOH, —COOR, —COCl, —CONH$_2$, —CF$_3$, —CCl$_3$, —CN, and —C(CN)$_2$, wherein R is selected from alkyl, allyl, benzyl groups, phenyl, and aryl groups.

3. The electro-polarizable compound according to claim 1, wherein the donor groups (R1) are selected from —O—, —NH$_2$, —NHR, —NR$_2$, —OH, —OR, —NHCOR, —OCOR, alkyls, —C$_6$H$_5$, and vinyls, wherein R is radical selected from alkyl, allyl, benzyl groups, phenyl, and aryl groups.

4. The electro-polarizable compound according to claim 1, wherein the at least one connecting group is a structure selected from structures: 13-22, where X is hydrogen (H) or an alkyl group:

13

14

15

16

17

19

20

21

22

5. The electro-polarizable compound according to claim 1, wherein the at least one connecting group is selected from CH$_2$, CF$_2$, SiR$_2$O, and CH$_2$CH$_2$O, wherein R is selected from H, alkyl, and fluorine.

6. The electro-polarizable compound according to claim 1, wherein the at least one connecting group is a structure selected from structures 24 to 29:

24

-continued

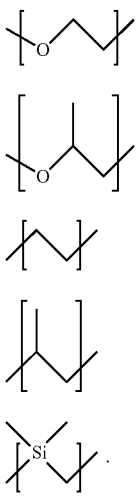

25

26

27

28

29

7. The electro-polarizable compound according to claim 1, wherein the resistive substituent R4 is selected from unsubstituted alkyl, unsubstituted aryl, substituted alkyl, substituted aryl, fluorinated alkyl, chlorinated alkyl, branched alkyl, branched fluorinated alkyl, branched chlorinated alkyl groups, and any combination thereof.

8. The electro-polarizable compound of claim 1, wherein the Core1 and the groups R1 and R1' form a non-centrosymmetric molecular structure.

9. The electro-polarizable compound of claim 1, wherein the Core1 the groups R1 and R1' and the resistive substituents (R4) form a non-centrosymmetric molecular structure.

10. The electro-polarizable compound of claim 1 having the following formula (II):

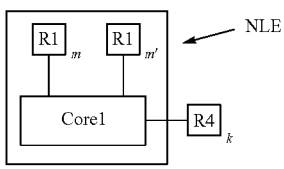

(II)

wherein the resistive substituents R4 are a non-conjugated part of compound II, and are either monocycles or fused polycycles, wherein the monocycles or polycycles are either saturated hydrocarbons or saturated halocarbons forming rigid spatial structures with dense packing of SP3 carbon saturated with H, F, Cl, and/or Br, and wherein k is a number of substituents R4 which is equal to 0, 1, 2, 3, 4, 5, 6, 7 or 8 and parameters n=p=s=0.

11. The electro-polarizable compound of claim 10, wherein a length of the non-conjugated part of the electro-polarizable compound is selected such that the resistivity of the electro-polarizable compound is greater than 1018 ohm cm.

12. The electro-polarizable compound of claim 10, wherein a length of the non-conjugated part of the electro-polarizable compound is selected such that the resistivity of the electro-polarizable compound is between 1018 ohm·cm and 1024 ohm·cm.

13. The electro-polarizable compound of claim 10, wherein the resistive substituent R4 is a polycyclic alkyl group and a polycyclic halo-alkyl group, wherein in the polycyclic halo-alkyl group is connected to the apex of Core1 on which the R1 is connected, or the apex of Core1 on which R1' is connected, but not both.

14. The electro-polarizable compound of claim 10, wherein the resistive substituent R4 is a resistive polycyclic substituent selected from $C_{25}H_{34}$, $C_{25}H_{35}$, $C_{25}F_{34}$ and $C_{25}F_{35}$ and located on the apex phenyl, naphthyl, or anthryl rings of Core1.

15. The electro-polarizable compound of claim 10 having the following formula (III):

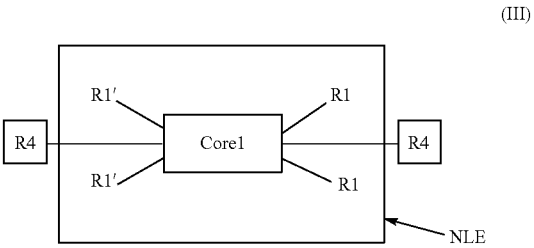

(III)

wherein R1' is an acceptor group, and R1 is a donor group.

16. The electro-polarizable compound according to claim 15, wherein the set of the electron donor and acceptor groups consists of two donor groups —$NH_2$ and two acceptor groups —$NO_2$, wherein m is equal to 4, located on rylene rings, or on apex phenyl, naphthyl, and/or anthryl ring positions of the Core1, or on both rylene rings positions and apex phenyl, naphthyl, and/or anthryl ring positions;
wherein the resistive substituent (R4) is an amine structure having a formula of the type:

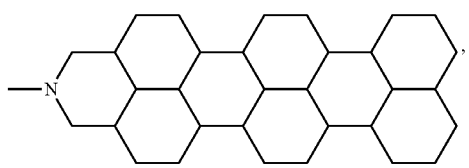 [SMILES: CN1CC2CCC3C4CCC5C6CCCC7CCCC(C8CCC(C9CCC(C1)C2C39)C4C58)C76]

wherein the resistive substituents R4 are connected the Core 1 via a connecting group.

17. The electro-polarizable compound of claim 10 having a formula (V):

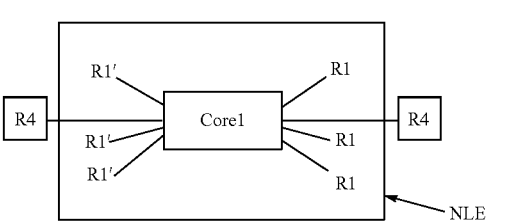

(V)

wherein the Core1 is the aromatic polycyclic conjugated molecule, R1 is a donor group, and R1' is acceptor group.

18. A solution comprising an organic solvent and at least one type of electro-polarizable compound according to claim 1.

19. The solution according to claim 18, comprising a mixture of different electro-polarizable compounds.

20. The solution according to claim 18, wherein the mixture of the electro-polarizable compounds comprises rylene fragments of different length.

21. The solution according to claim 18, wherein the organic solvent is selected from ketones, carboxylic acids, hydrocarbons, cyclic hydrocarbons, chlorohydrocarbons, alcohols, ethers, esters, and any combination thereof.

22. The solution according to claim 18, wherein the organic solvent is selected from acetone, xylene, toluene, ethanol, methylcyclohexane, ethyl acetate, diethyl ether, octane, chloroform, methylene chloride, dichloroethane, trichloroethene, tetrachloroethene, carbon tetrachloride, 1,4-dioxane, tetrahydrofuran, pyridine, triethylamine, nitromethane, acetonitrile, dimethylformamide, dimethyl sulfoxide, and any combination thereof.

23. A metadielectric layer comprising the electro-polarizable compounds according to claim 1, wherein the nonlinearly polarizable fragments comprising an aromatic polycyclic conjugated molecule with one or more R1 groups, and wherein the one or more R1 and/or R1' groups form a resistive envelope and solubilize the organic compound in a solvent and electrically insulating the column-like supramolecules from each other.

24. The metadielectric layer according to claim 23, wherein the column-like supramolecules are formed by the electro-polarizable compounds comprising rylene fragments of different length.

25. The metadielectric layer according to claim 23, wherein the metadielectric layer's relative permittivity is greater than or equal to 1000.

26. The metadielectric layer according to claim 23, wherein the layer's resistivity is greater than or equal to 1013 ohm/cm.

27. A meta-capacitor comprising two metal electrodes positioned parallel to each other and which can be rolled or flat and planar with said metadielectric layer between said electrodes, wherein the metadielectric layer comprises the electro-polarizable compounds according to claim 1 wherein the nonlinearly polarizable fragments comprising an aromatic polycyclic conjugated molecule with at least one group R1 or R1', the electro-conductive oligomers and the ionic groups which have electronic and/or ionic type of polarizability are placed into a resistive dielectric envelope formed by resistive substituents R1 and/or R1' providing solubility of the organic compound in a solvent and electrically insulating the column-like supramolecules from each other.

* * * * *